United States Patent
Shah

(10) Patent No.: US 9,906,870 B2
(45) Date of Patent: Feb. 27, 2018

(54) APPARATUSES AND METHODS FOR SOUND RECORDING, MANIPULATION, DISTRIBUTION AND PRESSURE WAVE CREATION THROUGH ENERGY TRANSFER BETWEEN PHOTONS AND MEDIA PARTICLES

(71) Applicant: Aalap Rajendra Shah, Kendall Park, NJ (US)

(72) Inventor: Aalap Rajendra Shah, Kendall Park, NJ (US)

( * ) Notice: Subject to any disclaimer, the term of this patent is extended or adjusted under 35 U.S.C. 154(b) by 0 days.

(21) Appl. No.: 15/089,306

(22) Filed: Apr. 1, 2016

(65) Prior Publication Data

US 2017/0238102 A1 Aug. 17, 2017

Related U.S. Application Data

(60) Provisional application No. 62/295,347, filed on Feb. 15, 2016.

(51) Int. Cl.
*H04B 10/00* (2013.01)
*H04R 23/00* (2006.01)
(Continued)

(52) U.S. Cl.
CPC ....... *H04R 23/008* (2013.01); *G01N 21/1717* (2013.01); *G01N 21/4795* (2013.01);
(Continued)

(58) Field of Classification Search
USPC ............................................ 398/40, 132–134
See application file for complete search history.

(56) References Cited

U.S. PATENT DOCUMENTS 3,175,088 A * 3/1965 Herriott .................. G02F 2/002
356/484
3,710,279 A * 1/1973 Ashkin .................. B01D 59/34
250/251

(Continued)

FOREIGN PATENT DOCUMENTS

| CN | 102723987 B | 8/2015 |
| JP | 2000162950 A | 6/2000 |
| WO | 2013051808 A1 | 4/2013 |

OTHER PUBLICATIONS

Yoshito Sonoda and Toshiyuki Nakamiya, Okai University, Kumamoto, Kumamoto 862-8652, Japan; "Proposal of Optical Wave Microphone and Physical Mechanism of Sound Detection"; AES 135th Convention, Convention Paper 8924; Oct. 17-20, 2013; pp. 1-8.

(Continued)

*Primary Examiner* — Agustin Bello
(74) *Attorney, Agent, or Firm* — Brosemer, Kolefas & Assoc., LLC

(57) ABSTRACT

Recording, manipulating, distributing and creating sound pressure waves in one or more media by employing an apparatus that transfers the energy between photons and particles of the media is disclosed. An exemplary apparatus comprises one or more lasers and an isotropic or anisotropic medium for photon processing and distribution. An exemplary method comprises determining the target locations for sound pressure wave recording, manipulating or creation; transmitting photons to the target locations; transferring photon energy to media particles to create or manipulate a sound pressure wave; or transferring energy of media particles to photons for recording or manipulating a sound pressure wave.

20 Claims, 13 Drawing Sheets

(51) Int. Cl.
  *H04R 1/20*     (2006.01)
  *H04R 1/42*     (2006.01)
  *H04B 10/114*   (2013.01)
  *G01N 21/17*    (2006.01)
  *G01N 21/47*    (2006.01)
  *G03H 1/02*     (2006.01)
  *G03H 1/04*     (2006.01)

(52) U.S. Cl.
  CPC ............. *G03H 1/02* (2013.01); *G03H 1/04* (2013.01); *H04B 10/114* (2013.01); *H04R 1/20* (2013.01); *H04R 1/42* (2013.01); *H04R 23/004* (2013.01)

(56) References Cited

U.S. PATENT DOCUMENTS

| | | | |
|---|---|---|---|
| 3,808,432 A * | 4/1974 | Ashkin | G21B 1/00 250/251 |
| 3,808,550 A * | 4/1974 | Ashkin | H01S 3/08 250/251 |
| 3,875,400 A * | 4/1975 | Pao | H04B 10/1121 359/285 |
| 4,011,445 A * | 3/1977 | O'Meara | G01S 17/89 342/179 |
| 4,361,911 A * | 11/1982 | Buser | G01S 17/74 342/45 |
| 4,641,377 A | 2/1987 | Rush et al. | |
| 4,731,879 A * | 3/1988 | Sepp | G01S 17/74 342/45 |
| 4,932,775 A * | 6/1990 | Wissman | G01S 17/32 356/28.5 |
| 5,192,979 A * | 3/1993 | Grage | G01S 17/50 342/192 |
| 5,206,504 A * | 4/1993 | Sridharan | H05H 3/04 250/251 |
| 5,220,328 A * | 6/1993 | Jehle | G01S 13/86 342/21 |
| 5,249,163 A * | 9/1993 | Erickson | G01D 5/30 359/223.1 |
| 5,262,884 A | 11/1993 | Buchholz | |
| 5,274,232 A * | 12/1993 | Chu | G01C 19/58 250/251 |
| 5,307,369 A | 4/1994 | Kimberlin | |
| 5,684,592 A * | 11/1997 | Mitchell | G01H 9/00 356/493 |
| 5,694,477 A * | 12/1997 | Kole | H04R 23/004 381/111 |
| 5,712,840 A * | 1/1998 | Matsumura | G11B 7/131 369/110.04 |
| 5,717,774 A * | 2/1998 | Kole | H04R 23/004 381/111 |
| 5,751,243 A * | 5/1998 | Turpin | G01S 7/20 250/370.08 |
| 6,014,239 A | 1/2000 | Veligdan | |
| 6,034,760 A * | 3/2000 | Rees | G01N 21/455 356/28.5 |
| 6,055,080 A | 4/2000 | Furstenau et al. | |
| 6,075,603 A * | 6/2000 | O'Meara | G01D 5/26 356/496 |
| 6,114,684 A * | 9/2000 | Mc Guire | H04K 3/822 250/208.2 |
| 6,147,787 A | 11/2000 | Veligdan | |
| 6,317,237 B1 * | 11/2001 | Nakao | G01H 9/00 398/130 |
| 6,434,239 B1 * | 8/2002 | DeLuca | G10K 11/1788 381/71.1 |
| 6,483,619 B1 | 11/2002 | Greywall | |
| 6,587,252 B1 * | 7/2003 | Bottrell | G02F 1/3515 359/246 |
| 6,590,661 B1 * | 7/2003 | Shnier | G01H 9/00 356/432 |
| 7,262,861 B1 * | 8/2007 | Pepper | G01B 11/06 356/502 |
| 7,577,260 B1 * | 8/2009 | Hooley | F41H 13/0081 381/307 |
| 7,630,646 B2 * | 12/2009 | Anderson | H04B 1/385 398/132 |
| 7,733,742 B2 * | 6/2010 | Gross | A61B 5/0059 367/191 |
| 7,751,716 B2 * | 7/2010 | Killinger | H04B 10/11 398/118 |
| 7,775,113 B2 * | 8/2010 | Bakish | G01H 9/00 398/130 |
| 7,949,259 B2 | 5/2011 | Suzuki | |
| 8,009,844 B2 * | 8/2011 | Whillock | H04B 10/11 345/158 |
| 8,131,154 B2 * | 3/2012 | Murayama | H04B 10/1141 398/118 |
| 8,286,493 B2 * | 10/2012 | Bakish | G01H 9/00 73/596 |
| 8,288,712 B2 * | 10/2012 | Bouyer | H05H 3/02 250/251 |
| 8,290,316 B2 * | 10/2012 | Molin | G01D 5/35303 250/227.11 |
| 8,301,029 B2 * | 10/2012 | Fischer | H04R 23/008 398/118 |
| 8,521,029 B2 * | 8/2013 | Pal | G01V 7/04 398/133 |
| 8,649,680 B2 * | 2/2014 | Okamoto | G02B 5/32 398/143 |
| 8,855,932 B1 * | 10/2014 | Lin | G01L 11/02 702/109 |
| 9,014,565 B2 * | 4/2015 | Sangawa | H04R 23/008 398/132 |
| 9,277,330 B2 * | 3/2016 | Aharoni | H04R 23/008 |
| 9,344,811 B2 * | 5/2016 | Bakish | H04R 23/008 |
| 2002/0030871 A1 * | 3/2002 | Anderson | H04B 1/385 398/132 |
| 2005/0083535 A1 * | 4/2005 | Kamshilin | G01H 9/00 356/502 |
| 2006/0109989 A1 * | 5/2006 | Linhard | G10K 11/28 381/160 |
| 2006/0139653 A1 * | 6/2006 | Chovan | G01H 9/00 356/484 |
| 2006/0241572 A1 * | 10/2006 | Zhou | A61B 8/12 606/7 |
| 2007/0041729 A1 * | 2/2007 | Heinz | G01B 11/303 398/25 |
| 2007/0081165 A1 * | 4/2007 | Kilic | G01H 9/004 356/477 |
| 2008/0034866 A1 * | 2/2008 | Kilic | G01H 9/004 73/514.26 |
| 2008/0037367 A1 * | 2/2008 | Gross | A61B 5/0059 367/8 |
| 2009/0203286 A1 * | 8/2009 | Murayama | A63H 3/28 446/27 |
| 2009/0225641 A1 * | 9/2009 | Sugita | G03H 1/265 369/103 |
| 2009/0257753 A1 * | 10/2009 | Fischer | H04R 23/008 398/133 |
| 2011/0071402 A1 * | 3/2011 | Masumura | G01N 21/4795 600/476 |
| 2011/0123199 A1 * | 5/2011 | Hashimoto | G01H 9/004 398/134 |
| 2012/0204649 A1 * | 8/2012 | Iwamoto | G01H 9/00 73/643 |
| 2012/0230687 A1 * | 9/2012 | Okamoto | G02B 5/32 398/44 |
| 2012/0243369 A1 * | 9/2012 | Sudo | A61B 5/0059 367/13 |
| 2013/0230329 A1 * | 9/2013 | Sangawa | H04R 23/008 398/133 |
| 2014/0153930 A1 * | 6/2014 | Fischer | H04R 23/008 398/133 |
| 2014/0241505 A1 * | 8/2014 | Xu | G01N 23/20066 378/87 |

(56) References Cited

U.S. PATENT DOCUMENTS

| | | | | |
|---|---|---|---|---|
| 2014/0353475 | A1* | 12/2014 | Meyers | G06N 99/002 250/216 |
| 2015/0077764 | A1* | 3/2015 | Braker | G01B 11/2518 356/620 |
| 2016/0354467 | A1* | 12/2016 | Bourke, Jr. | A23L 3/26 |
| 2016/0381071 | A1* | 12/2016 | Tatourian | H04L 63/18 726/23 |
| 2017/0238102 | A1* | 8/2017 | Shah | H04R 23/008 |

OTHER PUBLICATIONS

Gabriel Pablo Nava, Yutaka Kamamoto, Takashi G. Sato, Yoshifumi Shiraki, Noboru Harada, and Takehiro Moriya, NTT Communication Science Laboratories, Nippon Telegraph and Telephone Corporation; "Simultaneous acquisition of massive number of audio channels through optical means"; AES 135th Convention, Convention Paper 8965; Oct. 17-20, 2013; pp. 1-8.

A. Ashkin; "History of Optical Trapping and Manipulation of Small-Neutral Particle, Atoms, and Molecules"; IEEE Journal on Selected Topics in Quantum Electronics, vol. 6, No. 6; Nov./Dec. 2000; pp. 841-856.

Shahram Tehranian, Frank Giovane, Jürgen Blum, Yu-Lin Xu, Bo A.S. Gustafson; "Photophoresis of micrometer-sized particles in the free-molecular regime"; International Journal of Heat and Mass Transfer 44; Year 2001; pp. 1649-1657.

Evgenii E. Narimanov; "Photonic Hypercrystals"; Physical Review X 4, Apr. 10, 2014; American Physical Society; Year 2014; pp. 1-13.

Xiang Hao, Laure Martin-Rouault, & Meng Cui; "A self-adaptive method for creating high efficiency communication channels through random scattering media"; Nature, Scientific Reports; Jul. 29, 2014; 4 : 5874 | DOI: 10.1038, pp. 1-6.

International Search Report and Written Opinion of the International Searching Authority, International Patent Application No. PCT/US2017/017721, dated May 10, 2017.

Photorefractive effect—Wikipedia, https://en.m.wikipedia.org/wiki/Photorefractive_effect, printed Jun. 20, 2017.

A. M. Glass, The Photorefractive Effect, Optical Engineering, vol. 17 No. 5, Sep.-Oct. 1978, pp. 470-479.

P. Gunter et al., Introduction to Photorefractive Materials, Electro-optic and Photorefractive Materials, Springer-Verlag Berlin Heidelberg 1987, pp. 206-228.

* cited by examiner

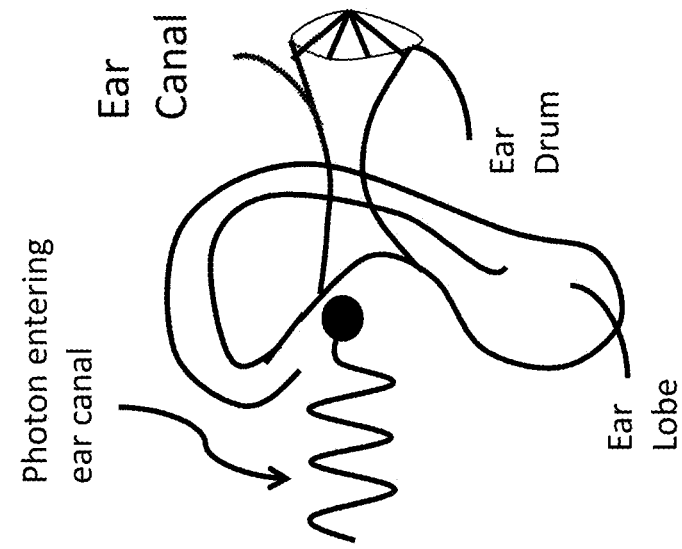
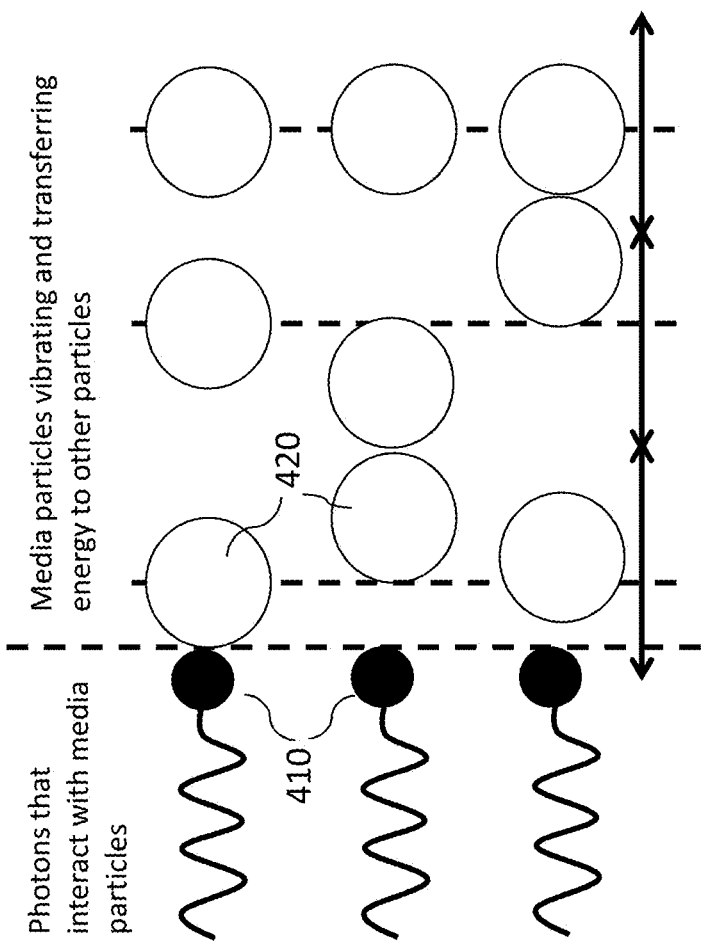
FIG. 4B
FIG. 4A

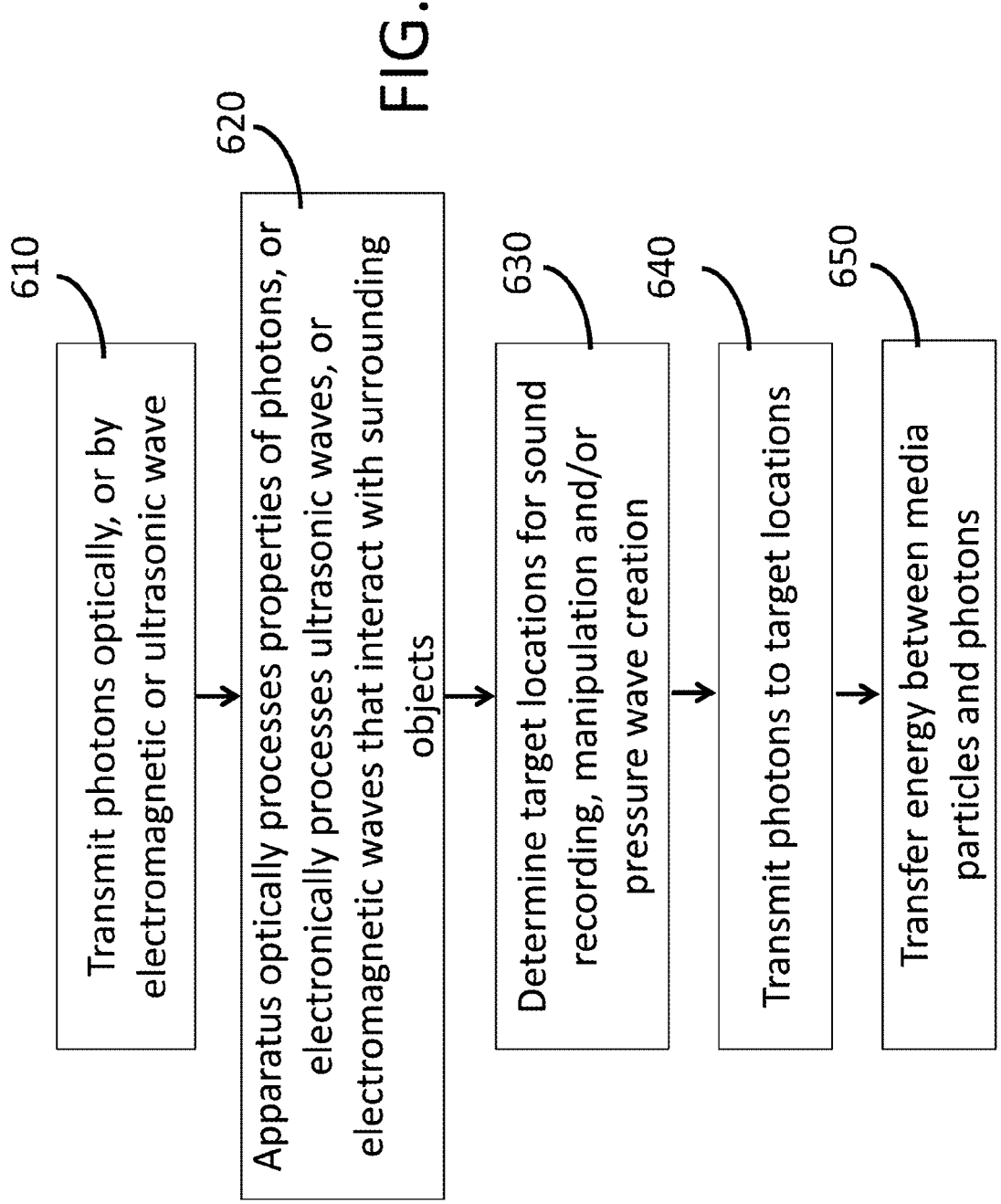

APPARATUSES AND METHODS FOR SOUND RECORDING, MANIPULATION, DISTRIBUTION AND PRESSURE WAVE CREATION THROUGH ENERGY TRANSFER BETWEEN PHOTONS AND MEDIA PARTICLES

RELATED APPLICATIONS

This Application claims priority from U.S. Provisional Patent Application No. 62/295,347, filed Feb. 15, 2016 and incorporated herein by reference in its entirety.

TECHNICAL FIELD

The present disclosure describes various apparatuses and methods relating to sound recording, creation, manipulation and distribution, involving the transfer of energy between photons and media particles.

BACKGROUND

Alexander Graham Bell and Sumner Tainter first demonstrated conversion of sound to light and light to sound in the 1880s with the invention of the photophone. The acoustic vibrations of a speaker's voice on a flexible mirror caused variations in the scattering of light by the mirror and the scattered light was converted into sound by a hard rubber diaphragm upon which the scattered light was incident; the sound was then amplified using a tube. Bell's observation that certain solid materials produced sound upon absorption of light (the rubber diaphragm in this case) later came to be known as the "photoacoustic effect".

The photoacoustic effect is the generation of sound waves in a material due to absorption of electromagnetic radiation. The primary cause is the varying expansion and contraction of material due to thermal effects, which results in the generation of a pressure wave. Spectroscopy, imaging and calorimetry are some of the widest applications of this effect. Attempts have been made to use the photoacoustic effect for other sound applications such as a speaker, e.g. U.S. Pat. No. 4,641,377.

The photoacoustic effect can only generate sound and does not result in the recording of sound, which limits its application. For medical and industrial ultrasonic applications and audio applications the drawbacks of this method are the expensive and cumbersome construction, the need for temperature and pressure control of the material, typically gas, and inadequate sound intensity so that sound generated for practical use outside the material must be coupled with the other medium and amplified.

Present day optical microphones are constructed so as to convert sound pressure waves into modulation of light properties such as phase, polarization or intensity. Typically, diaphragm displacement is detected with lasers and interferometry is used to determine changes in light properties after interaction with sound waves.

Other recent developments for sound recording attempt to overcome the limitations of conventional microphones that convert sound waves into vibrations of a diaphragm or plate. The diaphragm or plate that responds to sound pressure waves has a finite mass and size and takes a finite amount of time (delay) to respond to changes in sound wave pressure. The use of a diaphragm in conventional microphones results in non-linear distortion, limited frequency response, and limited dynamic range.

These recent innovations rely on the direct interaction of light with sound and use the effects of refractive index modification of air by sound pressure waves to measure modified light propagation which is determined by heterodyning the detected signal of a reference and signal laser beam. See, e.g. U.S. Pat. No. 6,014,239 and U.S. Pat. No. 6,147,787. In "Proposal of Optical Wave Microphone and Physical Mechanism of Sound Detection" by Yoshito Sonoda and Toshiyuki Nakamiya, incident laser light onto a sound wave gets weakly diffracted and is detected by an optical detector.

Drawbacks of the aforementioned approaches include expensive construction and calibration, complex optoelectronics to convert optical into electric signals and eliminate noise, and the dependence of microphone sensitivity on light path and hence device size.

Audio signals are conventionally carried in AM and FM radio waves through space and as electrical signals through wires. Some headphones and headsets are physically connected to the sound-generating device such as a computing device and constrain the location of the listener with respect to the device. Current wireless technologies for sound transmission include Bluetooth, Wi-Fi and other wireless technologies. The power required to transmit, receive and process the signals is significant, however, particularly for longer transmission ranges. Range is particularly limited for low energy transmission technologies.

Methods of transmitting optical signals over long distances use optical fiber to avoid electrical interference. See, e.g., U.S. Pat. No. 5,262,884, U.S. Pat. No. 6,055,080 and U.S. Pat. No. 6,483,619. Optical fibers have been used to eliminate common noise, radio frequency interference, electromagnetic interference and mains hum and to increase transmission distances. In most sound applications the microphone needs to be located away from the sound amplifiers and speakers. This requires the unamplified electrical microphone signals to be sent over long distances using cables. To support higher bit rates and wider bandwidth, point-to-point interfaces such as Ethernet, High Definition Multimedia Interface (HDMI) and optical fiber have been increasingly used to carry multiple signals along with other data. Jitter performance of Ethernet and HDMI affects sound quality. The length of the electrical cables is limited by electrical signal losses in the cable, capacitances and stray electromagnetic pick-up in the cable.

However, transmission over optical fiber entails a physical connection and requires conversion to electrical signals at the sound creation or storage location. The electro-optic conversion requires costly processing of the electrical signal at or near the place where the sound is captured. The optical signals after conversion to electrical signals need to be connected to a preamplifier before the signal can be amplified with a power amplifier. Moreover, for any wired distribution arrangement, the planning and layout of cables are critical and can become costly over large distances.

Other forms of electromagnetic radiation, including visible light, can also carry audio signals. "Simultaneous acquisition of massive number of audio channels through optical means", by Gabriel Pablo Nava, Yutaka Kamamoto, Takashi G. Sato, Yoshifumi Shiraki, Noboru Harada, and Takehiro Moriya, NTT Communication Science Laboratories, Nippon Telegraph and Telephone Corporation describes an optical system based on Visible Light Communication. The method for simultaneous recording of multiple audio channels and distributing the data employs LEDs and an imager to receive the data. Although theoretically thousands of channels can be recorded and transmitted, the paper explains the limitations imposed by hardware requirements for a high frame rate imager and sufficient image processing capability. This limits the scalability of the system. Other Visible Light Communication systems to transmit audio are described in, e.g., U.S. Pat. No. 8,131,154, U.S. Pat. No. 7,949,259, CN 102723987, US 20090203286, WO 2013051808.

The present disclosure sets forth below one or more implementations of sound distribution methods and/or apparatuses that avoid the problems of noise, poor jitter performance, and interference in distribution and that allow operation at much lower power than existing technologies for the same transmission distance.

Exemplary implementations in accordance with the present disclosure avoid the use of complex audio processing electronics and the associated drawbacks of known devices discussed above.

Laser-based photophoresis employs the radiation pressure force of laser light to impart momentum to media particles. Historically it has been used to manipulate particles, biological cells, atoms, and molecules in medicine, science and research. Photophoresis has applications in beam-powered propulsion in space, development of optical traps, and in the field of "atom optics" for manipulating media particles. "History of Optical Trapping and Manipulation of Small-Neutral Particle, Atoms, and Molecules", by A. Ashkin provides an introduction to the subject and a brief history.

As described below, embodiments of the present disclosure exploit laser-based photophoresis in a variety of applications in which sound is recorded, created and/or manipulated. A variety of such applications will now be discussed. Improved methods and apparatuses for transmitting sound are also described below.

SUMMARY

Exemplary implementations in accordance with the present disclosure relate to methods and apparatuses for recording, manipulating, transmitting and creating sound pressure waves using laser light for the transfer of sound pressure wave energy to photons (sound recording and manipulating), distribution of photons to target locations, and transfer of photon energy to media particles to create sound pressure waves (sound creation and manipulating). Manipulation of a sound pressure wave refers to modifying the properties of the wave such as amplitude, frequency, and phase. The sound pressure waves may be classified as any of the following: audible sound, infrasound and ultrasound.

Exemplary implementations in accordance with the present disclosure relate to methods and apparatuses for defining and creating zones, defined by one or more surfaces or bounded volumes, by directing photons in 3-dimensional (3-D) space to target locations that define the zones. By defining and creating these zones, the sound properties within them can be controlled.

Exemplary implementations in accordance with the present disclosure relate to methods and apparatuses for the detection and identification of objects for the purpose of determining target locations for distributing, recording, manipulating and creating sound pressure waves.

In one aspect, the present disclosure relates to microphones. In another aspect, it relates to loudspeakers, headsets, personal sound amplifiers and hearing aids. In another aspect, it relates to a method of generating pure 3-D sound. In another aspect, it relates to sound measurement systems. In another aspect, it relates to the transmission of sound in one or more media. In another aspect, it relates to the mixing and mastering of sound. In another aspect, it relates to sound production apparatuses such as musical instruments. In another aspect, it relates to noise reduction and cancellation. In another aspect, it relates to soundproofing. In yet another aspect, it relates to recording sound within defined regions in space. In yet another aspect, it relates to sound wave generation within defined regions in space. In yet another aspect, it relates to manipulating, eliminating and filtering sound at defined regions in space. In yet another aspect of the present disclosure, it relates to ultrasonic pressure wave creation, distribution and receipt of reflected and transmitted ultrasound pressure waves for applications including but not limited to medical and industrial applications.

Exemplary implementations in accordance with the present disclosure solve multiple problems in sound recording and reproduction by eliminating mechanical diaphragms and electronics employed during sound recording, manipulating and sound wave creation.

Exemplary implementations in accordance with the present disclosure solve multiple problems in transmitting sound by eliminating electromagnetic wave transmission and associated electronics and wires that would otherwise be required for sound distribution.

Exemplary implementations in accordance with the present disclosure enjoy the advantages of perfectly flat or near perfectly flat frequency response with little or no distortion, low noise, large dynamic range that is orders of magnitude greater than human hearing (resolution), frequency independent directionality, sound image location independence from speaker location and arrangement, very low latency, and low power consumption. It additionally reduces the physical footprint of present day sound devices that use current sound-based technologies, thereby enhancing the portability of such devices and the ease of use. A significant advantage is that mechanical and electrical design complexity are significantly reduced without sacrificing performance.

Exemplary implementations in accordance with the present disclosure provide greater flexibility and functionality in a single apparatus and can work in multiple physical media such as but not limited to air, water, living tissue, plastic and glass.

Exemplary implementations in accordance with the present disclosure make sound recording, distribution, manipulation, and pressure wave creation possible by exchanging energy between photons and media particles, thereby overcoming the above-mentioned problems with existing mechanical and electronic devices used in sound related applications.

In exemplary implementations in accordance with the present disclosure, some or all processing is performed in the optical (vs. electrical) domain, including: detecting the apparatus selection inputs; determining target sound recording, manipulation and creation locations; determining and applying required modifications to photon properties in order to modify sound properties; reading sound data encoded as properties of photons or optically encoded in an isotropic or anisotropic medium; detecting, classifying, recognizing and identifying objects; and determining how to interact with similar devices.

BRIEF DESCRIPTION OF THE DRAWINGS

FIG. 4A illustrates the exchange of energy between photons and media particles setting up vibrations in the media and resulting in sound generation.

FIG. 4B illustrates directing photons within the ear canal for energy exchange between photons and media particles inside the ear canal.

FIG. 6 illustrates a sequence for detecting target locations, distributing photons to these target locations and generating, manipulating and/or recording sound.

DETAILED DESCRIPTION

Figure 1:
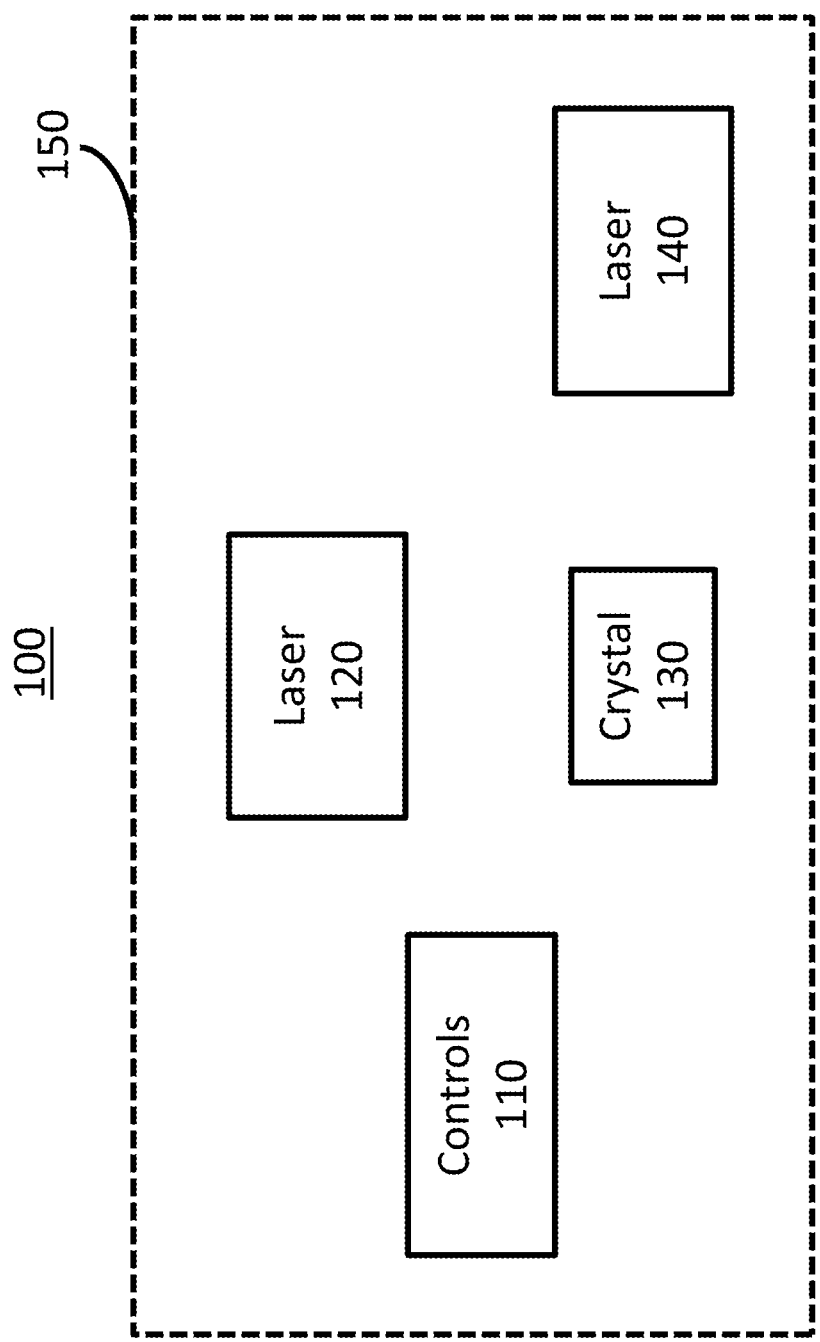
FIG. 1 is a simplified block diagram of an exemplary embodiment of an apparatus in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not be shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the Figures, including any functional blocks labeled as "processors" or "processing", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

FIG. 1 shows a block diagram of an exemplary optical apparatus 100 which may be contained in an optional enclosure 150. Optical apparatus 100 includes controls 110, a crystal 130, and two or more coherent light sources, such as lasers. Two lasers 120 and 140 are shown in FIG. 1. Lasers 120 and 140 are positioned to direct laser light toward crystal 130 so that the laser light beams emitted therefrom are mutually orthogonal with respect to their directions of propagation; i.e. the lasers 120 and 140 are positioned so that the axis of one beam is at a right angle to the axis of the other beam. This orthogonality can be exploited to obtain a specific phase and polarization relationship between photons in the beams. When two beams of laser light cross inside a type of nonlinear crystal, they mutually influence each other's propagation. In some cases, one beam will donate its photons to the other beam resulting in the nonreciprocal transfer of energy between the beams. The control of light by light is the optical analog of the control of electrons by electrons in transistors. The photorefractive effect is an effective optical nonlinearity in which the coherent interference of the two beams produces a pattern of bright and dark fringes. These fringes cause electrical charge to separate inside the photorefractive crystal, producing space-charge field patterns that mimic the light patterns. The electric fields, in turn, through the linear electro-optic effect, modify the refractive index of the material, creating a diffraction grating. This light-induced diffraction grating diffracts light from the two laser beams, redirecting the photons of one beam in the direction of the other beam. When the phase relationship is just right between the transmitted and diffracted beams, then net constructive interference will occur in one transmitted beam, but destructive interference will occur in the other beam. The photorefractive effect is the basis for dynamic holography. Holograms that move and change in time in response to changing light images are called dynamic holograms. They are recorded in real-time just as an ordinary hologram is, using two laser beams. One laser beam carries the information from the object, while the other laser beam acts as a reference. The use of two light beams rather than one (as in ordinary photography) makes it possible for a hologram to record phase as well as intensity. Dynamic holograms are constantly changing, or updating, as the information on the signal beam changes. As such, dynamic holograms produced in a crystal can perform an information processing function. In dynamic holography it is possible to simultaneously read and write a hologram in a photorefractive material.

Laser light photons from lasers 120 and 140 interact with crystal 130 resulting in the transfer of information from the crystal 130 to the photons or from the photons to the crystal. Space-charge field patterns inside crystal 130 serve as the means of storing information. While a crystal is shown in FIG. 1, crystal 130 may be replaced by other isotropic or anisotropic media in other embodiments. Crystal 130 can be implemented with photorefractive materials such as inorganic materials that include one or more of gallium arsenide (GaAs), barium titanate ($BaTiO_3$), lithium niobate ($LiNbO_3$), bismuth silicon oxide ($Bi_{12}SiO_{20}$), potassium niobate ($KNbO_3$), and strontium niobate ($SrNb_2O_6$), and organic materials that include one or more of a polymer, polymer composites, and amorphous composites. Other anisotropic materials that can be used also include liquid crystals, photonic crystals and various dielectrics. Semiconductors, like GaAs, can act as dynamic holographic media. They have high carrier mobilities that make the refresh rate of the holograms fast enough for audio and video applications. While birefringence is usually obtained using an anisotropic crystal, it can also result from an optically isotropic material in various ways such as deformation, suspension in another material, the Kerr effect, and temperature reduction to name a few. Some examples of isotropic materials include some polymers, glass, photonic crystals and isotropic liquid crystals.

Other embodiments may include other quantum memory storage techniques employing materials such as laser-cooled gases and trapped atoms, impurity-doped crystals, semiconductor materials, and optomechanical systems.

In an exemplary embodiment, one or both of lasers 120 and 140 can be implemented with laser diodes.

In operation, apparatus 100 transmits photons emerging from crystal 130 to one or more target locations. Sound pressure waves from an external source arriving at the target locations cause media particles at these locations to vibrate. The energy of the vibrations is transferred from the media particles to the photons at the target locations. From returning photons, apparatus 100 determines the change in photon properties resulting from the energy transfer and stores these properties in crystal 130 or in another medium (not shown) as optically encoded data relating to the sound pressure waves arriving at the target locations. The nonlinear paths of the returned photons in the crystal is indicative of the history of photon interactions.

In addition or alternatively to thus capturing or recording sound pressure waves at one or more target locations as described above, apparatus 100 can be used to create sound pressure waves at one or more target locations. In this case, apparatus 100 transmits photons that convey sound data in the form of photon properties to one or more sound pressure wave creation target locations. Energy of the photons transmitted to said target locations is transferred to media particles at the target locations to create sound pressure waves at the target locations in accordance with the sound data. Controls 110 can be used to define the sound properties of the resultant sound pressure waves that will be created by apparatus 100 at the target locations.

The aforementioned target locations, whether for sound capture or sound creation, can be defined using selection inputs of controls 110, by optically encoded data in crystal 130, or by automated discovery of target locations by the apparatus. Controls 110 may include mechanical controls (such as knobs, buttons, and sliders), electronic controls (such as a touchscreen), software controls, or optical controls (such as visible light, optical gestural interfaces, or holographic interfaces) or a combination of these controls. Controls 110 may be internal and/or external to apparatus 100. An exemplary implementation includes one or more mechanical switches, each of which controls the activation of a respective light source, such as an LED, thereby generating an optical signal based on a mechanical action. When photons of the optical signal arrive at crystal 130, the interaction of the electric field with the electric fields in the crystal can be used to determine the state of the control e.g. on or off. A sound property such as volume can be encoded in a bank of N LEDs (with $2^N$ combinations assuming that only on and off state of the LED is used as states for control). Another exemplary control mechanism may include a remote control that interfaces optically with apparatus 100.

Alternatively, instead of using controls 110, the definition of sound properties and/or target locations can be transmitted to apparatus 100 from one or more other apparatuses.

Figure 2:
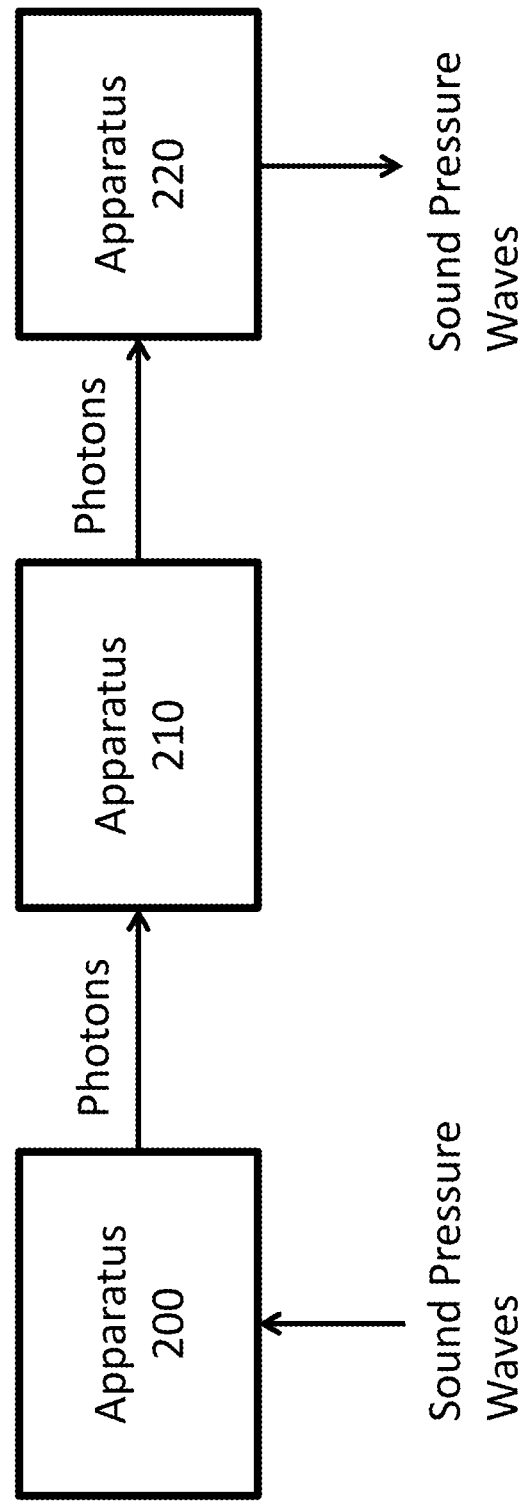
FIG. 2 is a simplified block diagram of an illustrative arrangement of a plurality of apparatuses used together to record, distribute, manipulate and generate sound pressure waves.

In an exemplary arrangement shown in FIG. 2, apparatus 210, which can be implemented using apparatus 100 of FIG. 1, receives optically encoded sound data, encoded as photon properties, from another similar apparatus 200. Apparatus 210 optically transmits the optically encoded sound data to apparatus 220 and prior to transmission may modify the properties of the optically encoded sound data. Apparatus 210 can be envisioned to be a repeater, amplifier, attenuator, mixing or mastering device, or any other device that can change the properties of sound. Apparatus 220, in turn, creates sound pressure waves by transferring the energy of photons to the media particles.

Any arrangement such as that of FIG. 2 can be implemented to allow apparatuses to communicate with each other and distribute the sound pressure wave recording, manipulating, distributing and creating tasks.

As mentioned, methods and apparatuses of the present disclosure exploit the exchange of energy between media particles and photons. The directed exchange of momentum between microscopic particles and photons has been described in "Photophoresis of micrometer-sized particles in the free-molecular regime", by Shahram Tehranian, Frank Giovane, Jurgen Blum, Yu-Lin Xu, Bo A. S. Gustafson [ix]. The photophoretic force and velocity on microscopic particles has been calculated in the free-molecular flow regime and for constant illumination. The phenomenon of directed momentum exchange is exploited in various implementations described herein for audio and other applications and in both directions: i.e., from photons to media particles and from media particles to photons.

Figure 3:
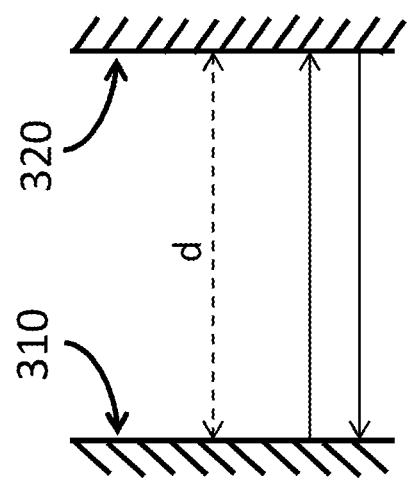
FIG. 3 illustrates the radiative exchange of energy between photons and a mirror for explaining photophoretic effects in implementations of the present disclosure.

The momentum exchange occurring between photons and media particles, also referred to as "energy exchange" or "energy transfer," will now be described in greater detail with reference to FIG. 3.

Photons have both wave and particle characteristics and observe wave particle duality. Though they have no mass, photons carry momentum, as described by the De Broglie equation, $p=h/\lambda$.

When photons are reflected, such as from mirrors, or interact with matter, an exchange of momentum takes place. At all stages, total momentum is conserved as in classical mechanics, even if the actual definition of momentum changes slightly and is not now equal to mass*velocity. Suppose then that a photon is bounced between two mirrors 310 and 320 arranged a distance d apart as shown in FIG. 3. The photon, traveling with speed c, the speed of light, travels distance d in time $t=d/c$. After leaving mirror 310, the photon travels to mirror 320, undergoes reflection at mirror 320, and then travels back to mirror 310. The time taken to return to mirror 310 is thus $t=2d/c$ and the photon strikes each mirror $c/(2d)$ times per second. Each time the photon strikes a mirror it transfers momentum equal to $h/\lambda-(-h/\lambda)=2h/\lambda$ to the mirror so the force exerted on the mirror is equal to the rate of change of momentum, $c/(2d)\times 2h/\lambda=ch/(d\lambda)$. The force exerted is very small. One photon with a wavelength of 10−10 m bouncing between mirrors 1 m apart exerts a force of 2*10−15 N.

The pressure exerted by photons is the principle behind the solar sail using the radiative pressure of photons. Photons from the Sun bounce off a large flat sail in space, pushing the sail away from the Sun. For sound related applications, when enough photons are directed towards a particle such as a molecule, the collective force can be used to vibrate the molecule. The oscillatory nature of the photophoretic force in a free molecular flow is obtained for certain values of the normalized size parameter and refractive index of the molecule. The vibrations in molecules can be adjusted by varying the direction and magnitude of the photophoretic force of photons at the impact area. A vibrating molecule produces similar vibrations in neighboring molecules, which do the same to their neighbors, and so forth, spreading the oscillations outward and leading to the creation of a sound pressure wave. FIG. 4A shows this phenomenon, in which photons 410 interact with media particles 420. If the photons are transferring energy to media particles, then each media particle in the path of energy transfer is displaced from its position and vibrates in a direction parallel to the direction of energy transport, thereby resulting in a pressure wave that is the sound pressure wave traveling in the medium.

FIG. 4B depicts photons distributed to an illustrative target location, in this case a person's ear canal. Once photons arrive at the ear canal, the photophoretic effect is produced inside the ear canal resulting in the generation of sound pressure waves.

In reverse to the phenomenon of imparting energy from photons to media particles, when a vibrating molecule imparts energy to photons, dampening of the molecular vibrational amplitude results. In reverse photophoresis, also illustrated by FIG. 4A, the transfer of energy is from media particles to photons. The use of both photophoresis and reverse photophoresis allows for energy to be imparted to and captured from media particles. Some embodiments of the present disclosure employ reverse photophoresis.

By employing a large number of photons in the momentum exchange with a single molecule and applying such a planned momentum exchange to many molecules, sound properties and direction of propagation or attenuation can be finely controlled. The photons employed for the transfer of energy with an apparatus of the present disclosure can be of any wavelength within the entire electromagnetic spectrum. Properties of sound including frequency, loudness, timbre, and/or phase can be encoded as photon properties. An exemplary apparatus defines the properties of photons prior to the exchange of energy with media particles or determines the properties of photons after the exchange of energy with media particles. In the former case, the apparatus imparts the sound properties encoded as photon properties to the media particles with which the photons interact. In the latter case, the apparatus detects from photons the sound properties imparted by the media particles to the photons with which the media particles interact.

Photons generated by an exemplary apparatus are transmitted to target locations in the media for sound recording, manipulation and generation. The target location information is stored in an isotropic or anisotropic medium such as crystal 130.

In other exemplary embodiments, target location information is stored in conventional memory, such as, for example, electronic digital memory. The digital data is read from the memory and converted to optical form, aka photons, so that the information can be processed by the dynamic holographic processor. The reading of digital memory and the digital-to-optical conversion processes will increase the latency of the system hence optical storage is preferred.

With reference to the exemplary apparatus of FIG. 1, the interaction of photons from lasers 120, 140 with crystal 130 results in linear or non-linear scattering effects and linear or non-linear propagation, with photons being distributed to the target locations. Examples of crystals that can be employed for non-linear effects include photonic crystals, meta-materials and photonic hypercrystals, such as described in "Photonic Hypercrystals" by Evgenii E. Narimanov. Crystals that produce linear scattering effects such as Diffractive Optical Elements can also be used. The crystal acts as a waveguide for the laser light. Several conventional approaches for non-mechanical beam steering include the use of holographic optical elements, liquid crystals and photonic crystals for dynamic time-varying optical path changes. These conventional techniques can be used to dynamically change the path of photons using crystal 130. Photons from crystal 130 are transmitted along various paths to arrive at a target location simultaneously. The simultaneous arrival of photons will result in the combined impact of photons at that target location.

A highly directional and efficient method of free space optical wave communication is described in "A self-adaptive method for creating high efficiency communication channels through random scattering media," by Xiang Hao, Laure Martin-Rouault, & Meng Cui. The method explains how to reduce the scattering effect of random scattering media on photons and how to achieve self-adaptive, non-linear photon path propagation. Such propagation can be advantageously employed for efficient communications in embodiments of this disclosure.

The benefits of the above described energy exchange between photons and media particles for sound recording, manipulation and creation are vast compared to conventional techniques. By eliminating mechanical diaphragms, electronics and cables, the sound quality of the original source is preserved. The following illustrate the capabilities of embodiments of the present disclosure.

Flat frequency response: The exchange of energy between photons and media particles introduces no distortion and is hence able to provide a flat frequency response. Unlike existing electronics-based systems, no microphone preamplifier related clipping or overloading is present.

Large dynamic range: Dynamic range is defined as the difference in Sound Pressure Level (SPL) between noise floor and the maximum SPL. The noise introduced in the energy exchange between photons and media particles is negligible. Since noise is nearly zero in this energy exchange, the dynamic range is a very large number, and many orders of magnitude greater than can be perceived by a human ear. The maximum SPL that can be achieved is many orders of magnitude higher than required for practical use.

Frequency range: The frequency range of sound that can be recorded, stored, manipulated, distributed and generated with embodiments of the present disclosure covers the entire sound spectrum from nearly zero Hz to the end of the ultrasonic frequency range. This is a significant improvement over any sound equipment including microphones, loudspeakers, mixers, and associated electronic components.

Directionality/Polar Pattern: Any polar pattern and directionality can be achieved for sound recording and pressure wave creation in accordance with the present disclosure. Because the precision of transmitting photons to target locations is extremely high, nearly perfect omnidirectional recording can be achieved. Directionality is not sound frequency dependent.

Channel Separation/Crosstalk: There is no crosstalk between sound channels; i.e. channel separation is infinite. This can be achieved since there is no common shared electrical signal. A set of discrete photons carries the sound data of a single channel.

Latency: Latency introduced by sound recording, distribution, manipulation and pressure wave creation depends on the speed of photons in the medium and the physical properties of the medium. For most common media such as air, water, animal tissue, plastic and glass, the speed of photons is relatively high and for most common applications the distances of transmission are small, such that latency is imperceptible by humans. This is a significant improvement in latency over digital systems. The latency experienced with embodiments of the present disclosure for recording, manipulating and creating sound pressure waves in air at nearby locations (e.g., within meters) would be on the order of picoseconds. Digital mixers, for example, exhibit an unavoidable amount of latency or propagation delay, ranging from 1.5 ms to as much as 10 ms, which can be disorienting and unpleasant to a user. Embodiments of the present disclosure do not require encoding in formats such as MPEG AAC, as long as the sound data is kept in the optical domain. This minimizes the processing required and minimizes latency.

Number of sound channels, sampling and bandwidth: Many photons are employed in the transfer of energy with a single particle or molecule and the transferred information will be carried by more than one photon. A collection of photons directed to a single target location (particle) will be encoded with sound properties for that location. The task of determining the sound properties of each collection of photons and subsequently encoding with sound properties these photons falls under the information processing function of the crystal. Since each collection of photons has properties independent of other collections, channel separation is maintained for sound generation. For sound recording, a similar technique is used wherein collections of photons are directed towards their target locations. After energy exchange with media particles, the returning collections of photons enter the crystal and the properties of the media particles are provided by the resultant non-linear paths of the photons in the crystal. The collections of photons can be distinguished from each other by their properties. The number of sound channels and bandwidth can thus be extremely large. Sampling is actually performed at the rate at which the media particles can be displaced. Due to the large bandwidth and number of channels, a sound pressure wave can be perfectly replicated and apparatus in accordance with the present disclosure can record, manipulate, distribute and create sound pressure waves for a true 3-D sound image.

Distribution losses and noise: Exemplary embodiments of the present disclosure use photons to transfer sound from one location to another. Sound distribution via photons is an efficient transmission process. Common noise, radio frequency interference and mains hum have no impact on the sound. Exemplary embodiments eliminate the need for a sound reinforcement system that is complex and costly. The photons can be transferred using multiple optical repeaters to the desired sound wave creation locations with minimal transmission losses.

Storage medium read and storage rate: Large data rates can be accomplished for storing and retrieving information from optical storage media since the store and read rates are on the order of the speed of light.

Flexibility: The location of a generated sound image can be varied without changing the location of the apparatus generating the sound image. This is a significant improvement over current loudspeakers that are fixed in position or ultrasonic transducers that must be moved over a patient's body. Significantly greater control in sound recording, manipulation and creation can be provided with a single apparatus, including the ability to vary the location of sound recording, manipulation and pressure wave creation without changing apparatus location, and the ability to provide continuous instead of discrete variation in the polar pattern. Exemplary embodiments also have the flexibility to work in more than one media, such as but not limited to air, water, plastic, human tissue and glass.

Power consumption: The power required to record sound, distribute photons and create sound pressure waves is provided by the power source that is driving the lasers. The energy transfer process between media particles and photons is highly efficient and can be finely controlled. The power required by exemplary apparatuses to perform the same function is much lower than conventional recording, distribution and loudspeaker devices.

Cost: The elimination of electronics for sound recording, manipulation and pressure wave creation and the elimination of distribution equipment such as amplifiers and cables result in lower cost and complexity of exemplary sound equipment. A single apparatus can provide significant flexibility to control the recording, distribution, manipulation and generation of sound.

Size and Packaging: Exemplary apparatuses can be made more compact than currently available electronic apparatuses of similar functionality. No special packaging, such as with MEMS technology and loudspeakers, is required with exemplary apparatuses since all transduction occurs in the medium between photon and medium particles, and no special protection is required from radiated disturbances for sound distribution.

Other types of electronic and optical apparatuses, such as, but not limited to, mobile phones, desktop computers, laptop computers, tablet computers, media players, televisions, gaming devices, cameras, video recorders, positioning devices, electronic books, wearable devices, projector devices, vehicles, analog and digital sound equipment and other types of electronic and optical systems, may be implemented in accordance with the present disclosure.

Figure 5:
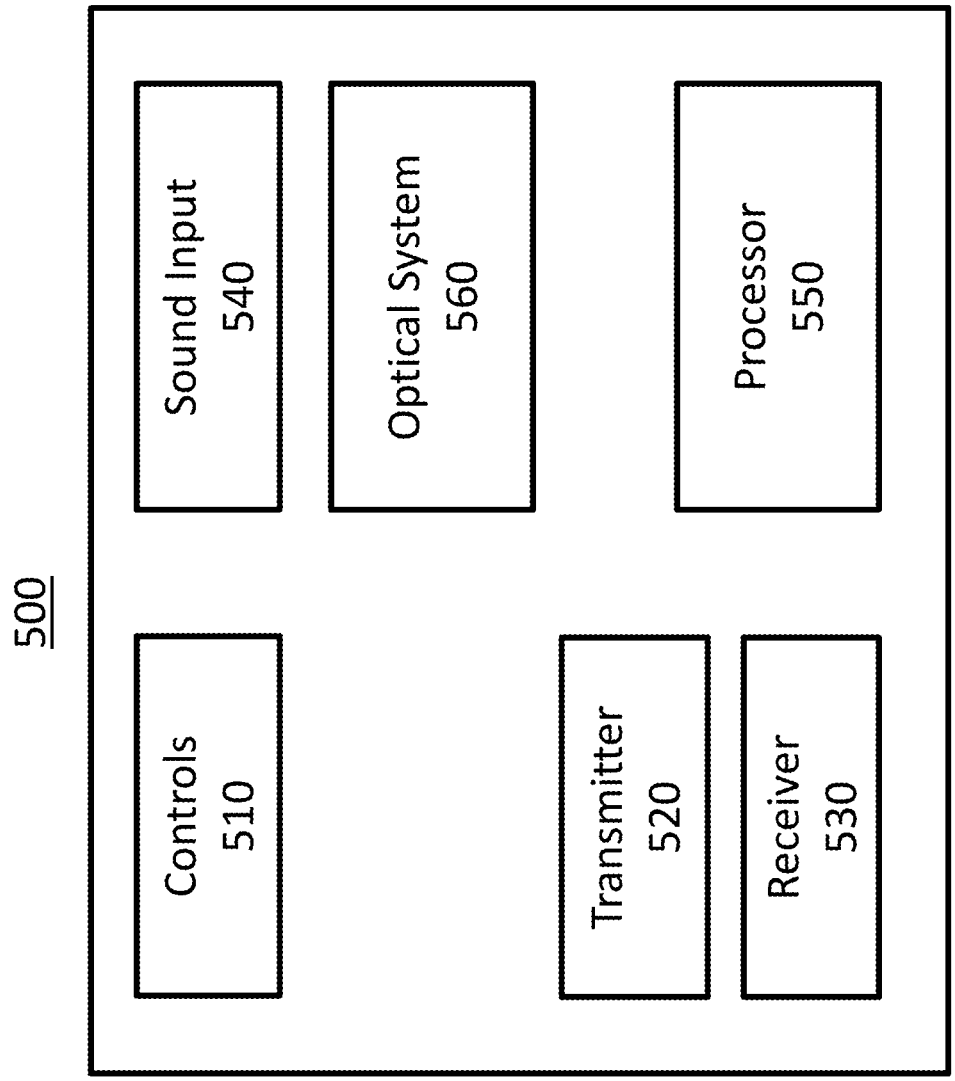
FIG. 5 is a simplified block diagram of an exemplary embodiment of an apparatus including components for using ultrasound, electromagnetic waves or laser generated photons to determine target locations for sound pressure wave recording, creation or for manipulating sound properties.

FIG. 5 shows a block diagram of an exemplary apparatus 500 comprising an optical system 560 which can be implemented with apparatus 100 of FIG. 1. Apparatus 500 may have its own set of controls 510 in addition to or instead of the controls 110 from FIG. 1. Apparatus 500 includes an electronic transmitter 520 and receiver 530, which in exemplary embodiments transmit and receive ultrasonic or electromagnetic waves (e.g., radio or terahertz frequency) that are used for determining target locations for sound recording, manipulation and pressure wave creation. Electromagnetic wave transmission, reception and processing is distinguished from photon based transmission, receiving and processing in that electromagnetic wave receivers, transmitters and associated processing require electronics, whereas photon based distribution, receiving and processing do not. As such, one or more components of apparatus 500 can be implemented in electronic, opto-electronic or all-optical forms. Transmitter 520 and receiver 530, which are shown as separate components, may be combined into a single component.

The return ultrasonic or electromagnetic waves received by receiver 530 are processed by processor 550 to detect and determine the locations of surrounding objects and to perform pattern recognition so as to identify detected objects. For example, the body and facial features of persons, especially substructures of the ears, such as the pinna, ear canal, ear-drum, cochlea or cilia, are located and tracked by the apparatus. These are known target locations for sound pressure wave creation. Such features can further be associated with and identified as belonging to specific persons. Other structures of the body such as the mouth can be located and tracked for sound pressure wave recording, while the pelvis, legs, arms, neck, abdomen and other structures can be assigned as reference locations which can be used to define target locations for sound creation, manipulation and creation. These target locations may be used for ultrasonic sound pressure wave creation as administered during ultrasound imaging and medical procedures. Other features of objects including but not limited to shapes, edges, and surfaces can be used for object classification.

Processor 550 estimates individualized Head Related Transfer Function (HRTF) from return data (such as ultrasonic or electromagnetic wave return), generates and refines HRTF estimations and target location estimations by learning over multiple ultrasonic returns, and employs a classifier to classify features of objects. The return from objects, including walls, is used to estimate reverberation effects and the locations of the objects. Optical system 560 receives the target location information from processor 550 over an optical, wired or wireless interface.

Processor 550 may perform any other processing besides that described above. The processor can include any analog, digital or hybrid electronic circuit and combination of circuits, the primary function of which is to process the data received from receiver 530 and optical system 560. The processor can include any integrated circuit such as a Field Programmable Gate Array (FGPA), Application-Specific Integrated Circuit (ASIC), a Central Processing Unit (CPU) or combination of such processors.

Apparatus 500 includes a sound input component 540 that receives an electrical input signal representing sound, such as over a physical connector or over the air using a wireless link such as Bluetooth or Wifi. The signal is then sent to processor 550 for processing, including but not limited to channel separation, modeling of 3-D sound field, modeling of reverberation effects, HRTF and other transfer function corrections, correcting for reverberation effects, and adding sound effects or changing the sound frequencies, loudness, timbre, or phase and any combination thereof, based on the settings of controls 510. The processed sound data is transmitted from processor 550 to optical system 560 by photons over a wired or wireless interface.

Controls 510 are similar to controls 110 in FIG. 1. The controls can be used to define target locations (including zones which are a collection of target locations) in which, or at the boundaries of which, sound pressure waves are recorded, manipulated and/or created. The controls can also used to define the properties of sound pressure waves that travel across the boundaries of and within a defined volume or zone.

Once the necessary processing of sound data is complete, optical system 560 transmits photons to the target locations, where the energy transfer between photons and media particles can take place from photons to media particles, media particles to photons or both. The sound input from 540, or sound transmitted to the apparatus from another optical apparatus, such as depicted in FIG. 2, or sound stored internally in apparatus 560 is distributed by the photons and then pressure waves are created at the target locations. For sound recording, the photons at the target locations are imparted with energy from media particles at the target locations.

The transmit and receive functions of 520 and 530 can also be performed by optical system 560, in another embodiment in which the transmitted waves, such as ultrasonic waves, are generated using the lasers and isotropic or anisotoropic material, and the received waves are converted back to photons. In this exemplary embodiment, optical system 560 generates and receives ultrasound by transferring energy from photons to media particles (transmitter operation) and from media particles to photons (receiver operation). The photons obtained from the receiver operation are then optically processed by processor 550, which in this embodiment is an optical processor (or computer) and is able to detect and classify surrounding objects.

In another embodiment, photons from optical system 560 are transmitted directly to the surroundings and optical system 560 receives the photon return. Processor 550 processes the received photons, and based on the received photon properties, surrounding objects are detected and classified. If the apparatus is constructed as a true optical device (i.e., without electronics for transmission, receiving and processing), then the components 520 and 530 are not required as 550 and 560 perform all the electronic functions in the optical domain.

Benefits of embodiments of the present disclosure will now be discussed.

Minimal Soundproofing and Noise Reduction: The ability to locate ears and create sound pressure waves at the ears means that reverberation effects are reduced significantly for listeners. This minimizes the need for noise barriers, sound baffles and anti-noise sound generators. Similarly, the ability to record sound at the mouth location reduces the amplitude of unwanted surrounding noise.

Ease of use: Locating and tracking ears eliminates the need to wear headsets, earphones and other sound devices worn over ears. Similarly, since mouths can be located and tracked, the apparatus eliminates the need to wear or hold microphones.

Listener and Speaker Location Flexibility: Real-time tracking of the listener or speaker (animate or inanimate) allows the location of the speaker or listener to change relative to the apparatus, and the apparatus need not be in the immediate vicinity of the speaker or listener.

Real Time Sound Recording, Distribution and Power Efficiency: The ability to determine the real-time locations of listeners and speakers (animate or inanimate) can be used to determine locations for sound pressure wave creation, manipulation and recording. Locations between the apparatus and speakers or listeners that do not require sound pressure wave creation or recording can be excluded as target pressure wave creation and recording locations. This provides power consumption efficiency in sound creation, distribution, manipulation and recording.

FIG. 6 depicts an exemplary method for determining target locations, transmitting photons to the target locations, and recording, manipulating or creating sound pressure waves. A target location may be any location, including a location where a living object or part of it is present, including but not limited to humans, animals, and plants; or a location where a non-living object is present, including but not limited to a repeater, router, recording or loudspeaker device. FIG. 6 illustrates the use of electromagnetic waves, ultrasonic or photon transmission at 610, receipt of the return at 620, and processing of the return at 630 to detect sound recording, manipulation and pressure wave creation target locations, such as the locations of a listener's mouth or ears, for example. At 640, photons are transmitted to the target locations. At 650, energy is exchanged between photons transmitted to the target locations and media particles.

When the objects for which target locations are defined move or the apparatus moves, the apparatus continues to transmit and process returns so that the relative or absolute locations of the living or non-living object are tracked in real time. Tracking of ears or lips (or mouth) of a person is performed especially when a recording or creation volume has been defined as described below.

In another embodiment, sound is distributed to one or more target locations by detecting an object and determining target sound pressure wave creation locations with reference to the object. The object being detected can be one or more, partial or whole, animate or inanimate objects and the zone can be defined in relation to the detected objects. An example of this embodiment uses an object such as a human head or the walls of an auditorium. In this example, faces or heads can be used for determining the approximate locations of ears and a target location for sound recording and pressure wave creation can be determined relative to the location of the ears. Similarly, walls can be defined as the object such that all target locations are within the confines of the walls. The target locations for sound pressure wave recording, manipulation and creation may be distributed in space relative to the objects. At the distributed target locations, sound pressure wave creation would allow all objects to receive the sound pressure waves. The same approach is used to record sound from multiple sound generating objects by recording sound at distributed target locations.

In another embodiment of this method, the target locations are distributed in the media at numerous locations based on a 3-D model of the sound field such that the sound recorded is 3-D sound or the sound synthesized at each target location gives the listener an immersive 3-D experience. Exemplary apparatus may define the volume size and shape of the 3-D sound field based on the locations of objects.

Although described in various embodiments and illustrated in FIG. 6, this method does not necessarily require the detection of listener and speaker locations by the apparatus. Instead, a user may manually define the target locations for sound pressure wave creation, modification or recording by the apparatus provided controls.

Figure 8:
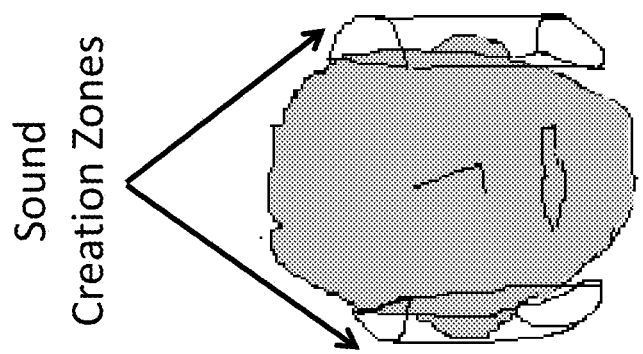
FIG. 8 is an illustration of a defined volume used as a sound recording zone.
Figure 7:
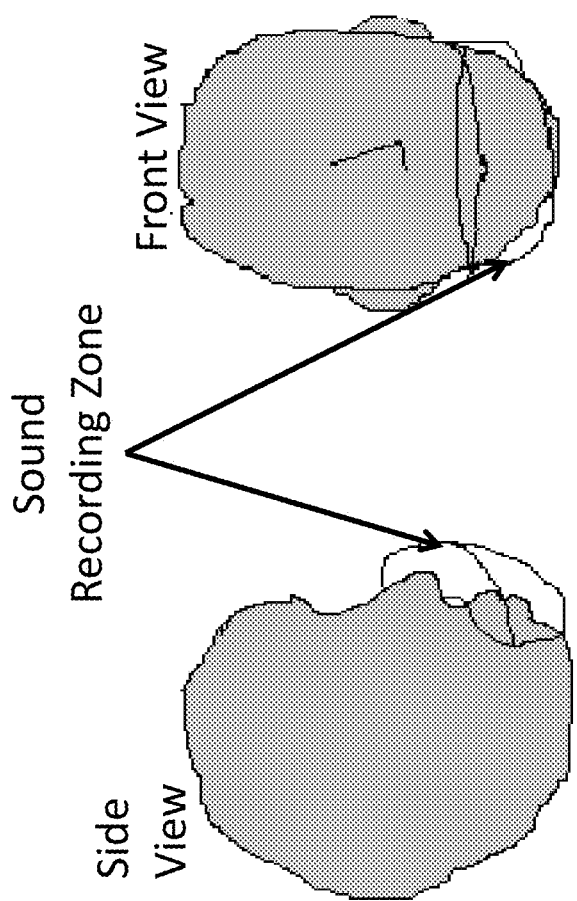
FIG. 7 is an illustration of a defined volume used as a sound creation zone.

FIG. 7 shows an illustrative recording zone that is defined around a person's mouth. FIG. 8 shows sound creation zones that are defined around the ears. Each of the zones can be defined as one or more surfaces or a volume. If a zone boundary is defined by a surface or plurality of surfaces that do not enclose a volume then the defined zone can extend indefinitely. In another scenario, the surface or plurality of surfaces can form an enclosed volume by intersection with physical objects such as the walls of a building.

A recording zone, such as depicted in FIG. 7, is a zone where energy of sound pressure waves is transferred to photons for recording. A sound creation zone, such as depicted in FIG. 8, is a zone where energy of photons is transferred to media particles to create sound pressure waves. The properties of sound at the boundaries of a recording or creation zone can be controlled such that properties of sound waves crossing the boundary into or out of the zone are varied as the sound waves cross the boundary. Zones can be created for audible as well as inaudible sound (i.e., infra- or ultrasound).

A manipulation zone is a type of zone for the manipulation of sound properties, and may or may not involve the creation or recording of sound pressure waves. An example of a manipulation zone is a silence zone, in which sound creation or the transmission of sound therein is restricted by photons absorbing all the energy of surrounding media particles at the boundaries of the zone. An effective means of noise insulation is the creation of an insulating layer by pushing the media particles away from each other on opposite sides of an imaginary plane or complex surface. This requires much less power than active noise cancellation since the power required for active noise cancellation is equal to the power of the oncoming sound pressure waves.

A manipulation zone can be defined such that it is applicable to only certain types of sounds, the properties of which meet defined criteria. The criteria can be defined so as to result in noise cancellation. The sound properties may be defined for either specific portions of the boundary of the zone, the oncoming sound pressure waves, the outgoing sound pressure waves or a combination of these.

The controls (110, 510) of the apparatuses (100, 500) can be used to define zones associated with an object by defining features of the object, such as its shape or size. Detection may also be performed based on a predefined object whose definition is stored in crystal 130, such as a mouth object shown in FIG. 7 and ear objects shown in FIG. 8. Upon detection of an object such as a mouth or ear, zones are established by propagating photons to locations relative to the object. Optical system 100 uses the inputs of controls 110 to determine the physical region in 3-D space (zones) where sound pressure wave energy is ether controlled along the boundaries of the defined volume, within the volume or along the set of defined surfaces. Using non-collinear photon propagation, a complex shaped zone can be created conforming to a predetermined shape or the complex zone can be created as a dynamically varying shape. The detected objects may become references for defining the zone boundary, i.e. the zone boundaries can be different from the object boundaries.

A user may place the apparatus near the object to be detected to increase the probability of accurately locating the object and defining the zone.

The apparatus controls the sound properties across the boundaries and inside the zone for recording, manipulation and sound pressure wave creation. The apparatus accomplishes this by modifying one or more sound properties, including, but not limited to, amplitude, pressure, intensity, frequency, speed, direction, phase and timbre.

Figure 9:
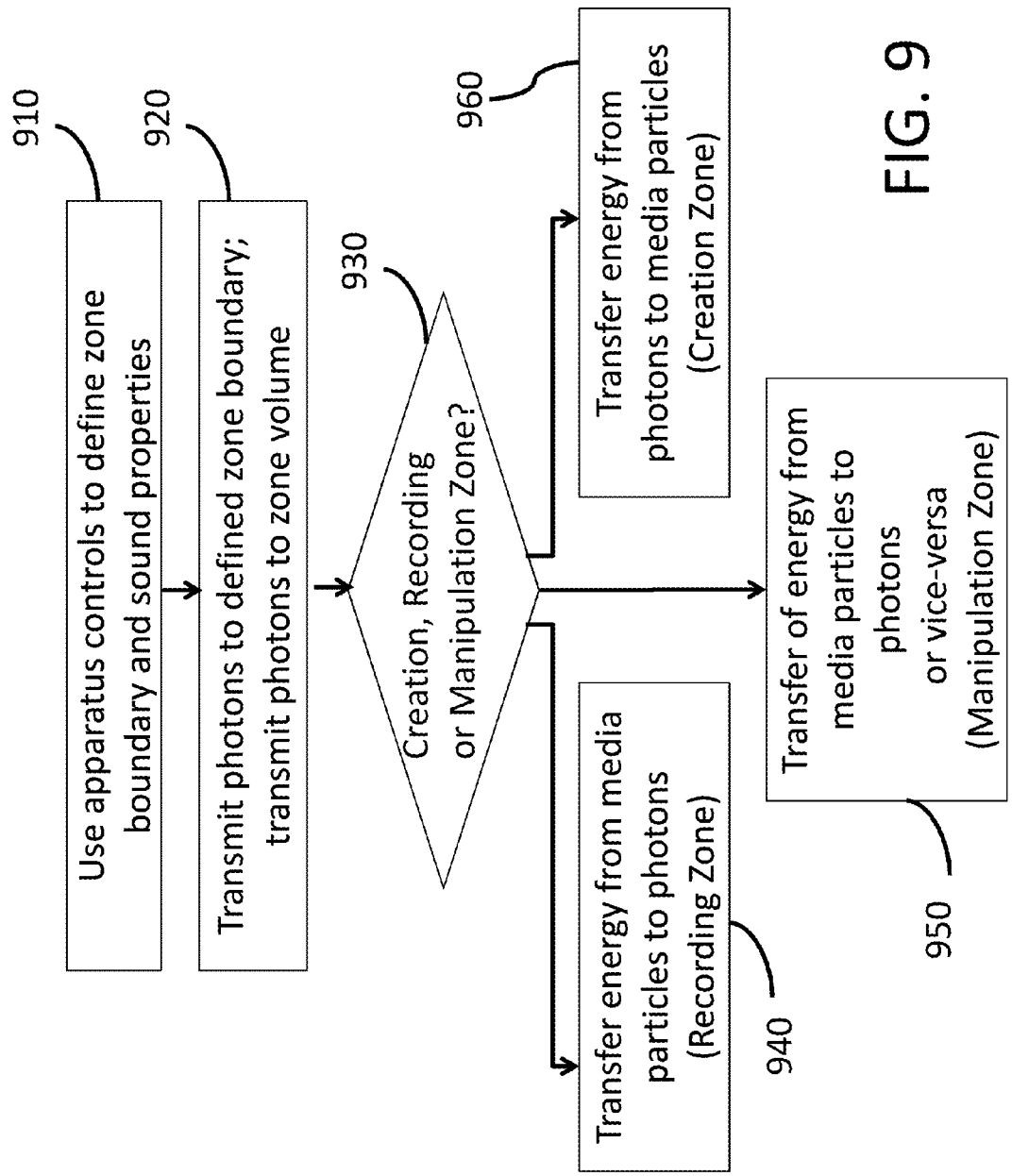
FIG. 9 is a sequence for defining and controlling sound properties across volume boundaries.

FIG. 9 illustrates an exemplary method for generating and using sound recording, manipulation and creation zones. At 910, zone boundaries are defined using the apparatus controls. At 920, the apparatus transmits photons to the boundary of the defined zone or to the entire volume of the zone. Depending on the type of zone as determined at 930, energy is transferred between the media particles and the photons, at 940, 950 or 960. In the case of a recording zone, energy is transferred at 940 from media particles to photons. In the case of a manipulation zone, energy may be transferred at 950 from media particles to photons, from photons to media particles or both. In the case of a creation zone, energy is transferred at 960 from photons to media particles. The energy transfer that takes place is such that the resulting sound from the energy exchange has the properties that were defined for the zone in 910.

Precise measurements of sound properties within a recording zone can be accomplished by preventing noise surrounding the zone from entering the zone along the zone boundary. This makes exemplary apparatuses extremely efficient in measuring sound pressure level or other sound properties, such as may be performed when operated as a phonometer.

Several benefits of exemplary apparatuses will now be discussed.

No physical materials for soundproofing are needed. Instead, photons are transported to the zone boundaries or to locations within the volume of the zone. This provides an easy, low cost approach that is not possible with existing soundproofing or noise reduction measures. It can be used in applications where space or weight constraints restrict the use of physical materials. Present devices for noise control require physical materials in order to constrain or eliminate the sound.

A zone can be defined using a volume or surface of any 3-dimensional complexity.

The apparatus provides the flexibility to modify the zone boundary and the sound properties of the zone using the apparatus controls. This does not require movement of any physical materials such as soundproofing materials.

Figure 10:
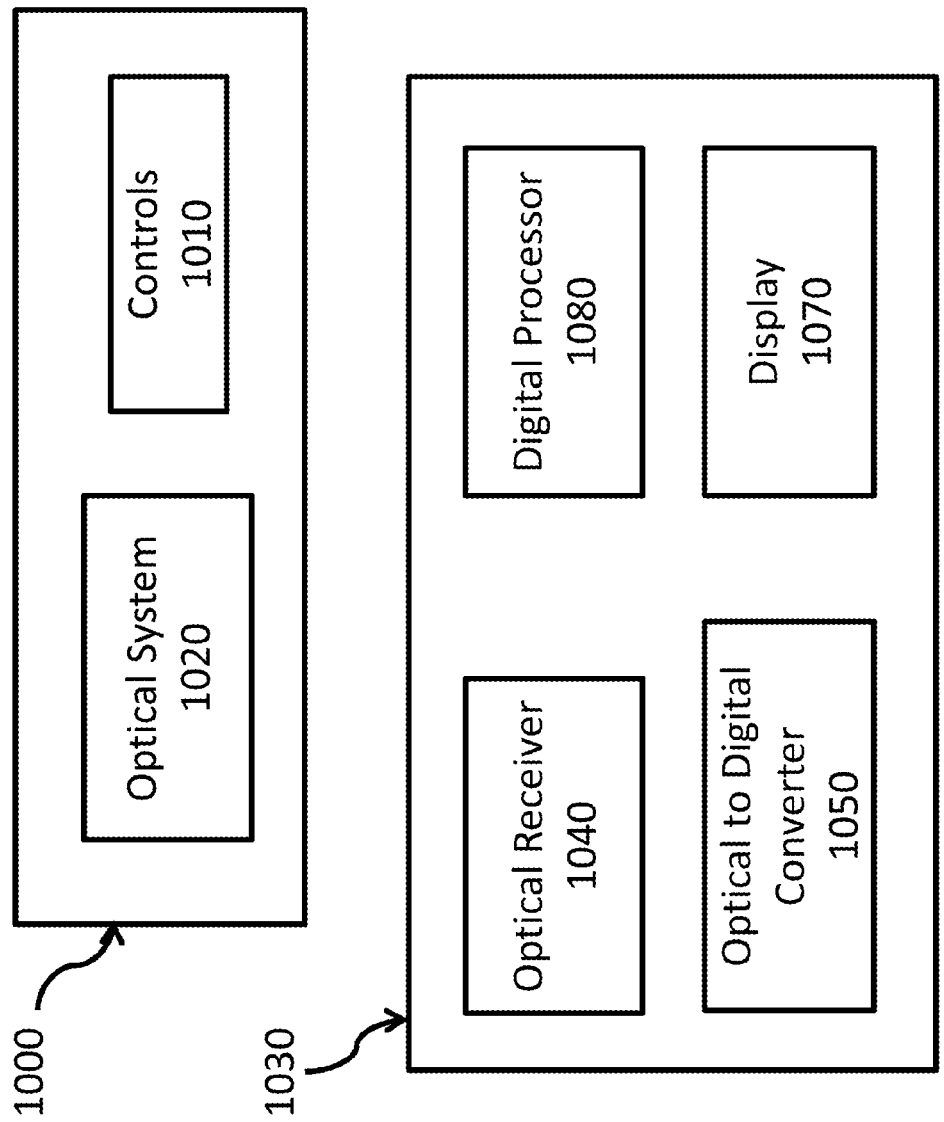
FIG. 10 is a simplified illustration of an exemplary apparatus that includes, in addition to optical transduction and distribution components, components for receiving, performing optical to digital conversion and processing reflected ultrasonic pressure waves and displaying data.

FIG. 10 shows a system 1000 for generating and processing ultrasonic pressure waves that includes an optical system 1020, such as optical apparatus 100 of FIG. 1. Controls of system 1020 or additional controls 1010 are used to define the location and size of the ultrasonic pressure wave creation and recording zones, which may otherwise be pre-encoded in the crystal of optical system 1020. In addition to the modes and methods of scanning, controls 1010 are used additionally to change properties of the ultrasonic wave, including but not limited to: intensity, beam angle, beam spread, center frequency, bandwidth, and pulse width. Optical system 1020 directs photons to the target locations, and causes the photons to transfer energy to the surrounding media particles to generate ultrasonic sound pressure waves. The energy of the reflected or transmitted ultrasonic waves is transferred back to photons at the target sensing locations. The target sensing and pressure wave creation locations may be the same or different locations. The ultrasonic scan data is processed using photon based optical processing and the processed data can be presented on a display as a hologram.

FIG. 10 also shows an optical receiving and digital display system 1030, which is an optional system that can interact with system 1000. An optical receiver 1040 of system 1030 receives photons carrying ultrasonic and other unprocessed or processed data from system 1000 and converts the optical data to a digital signal using an optical to digital signal converter 1050. The digital signal is sent to the digital processor 1060 that processes the raw data and may further process pre-processed data from system 1000. The processed data is sent to an electronic display 1070 where the processed ultrasonic scan data is displayed.

For therapeutic applications such as ultrasonic heating, system 1000 may be used alone. The combination of systems 1000 and 1030 may be used for displaying images while other processes such as ultrasonic based heating are performed by system 1000. For applications such as but not limited to elastography, where multiple ultrasonic pressure waves having different properties are transmitted and received, system 1000 is sufficient to produce all the required ultrasonic pressure waves. However, system 1000 can also transmit photons to one or more other optical systems like system 1000, which would also generate ultrasound pressure waves at the same or different target locations. This is similar to the concept shown in FIG. 2.

Optical system 1000 records the ultrasonic data received via energy exchange between photons and reflected ultrasonic waves by storing this data in its crystal. The data stored optically can be processed and displayed at the time of recording the data or any time during or after which ultrasonic pressure waves are created and received.

For endovaginal, endorectal, transesophageal and other applications within the body, an exemplary embodiment of optical system 1000 can be mounted on a small diameter catheter or other means and placed into the body such as through blood vessels to image the walls and disease of those vessels. Optical system 1000 can communicate via photon transmission with system 1030, which resides outside the patient's body.

The benefits of this embodiment for medical and industrial applications are similar to those described earlier for system 100. A single apparatus 1000 can be used as both the transmitter and receiver and as one or more transceivers. A coupling medium is not required and the apparatus does not need to be in contact with the material or body receiving the ultrasonic pressure waves, hence the use of the ultrasonic apparatus is less reliant on operator skill and does not pose a risk of infection or contamination. The apparatus provides a flat response over a wide frequency range, and compared to other types of transducers can provide a larger frequency range, larger dynamic range, larger maximum pressure output, better receive sensitivity while providing a high coupling efficiency, and higher signal to noise ratio. The number of channels can be much higher than the 96 to 512 channels used today, thus providing higher imaging quality.

Figure 11:
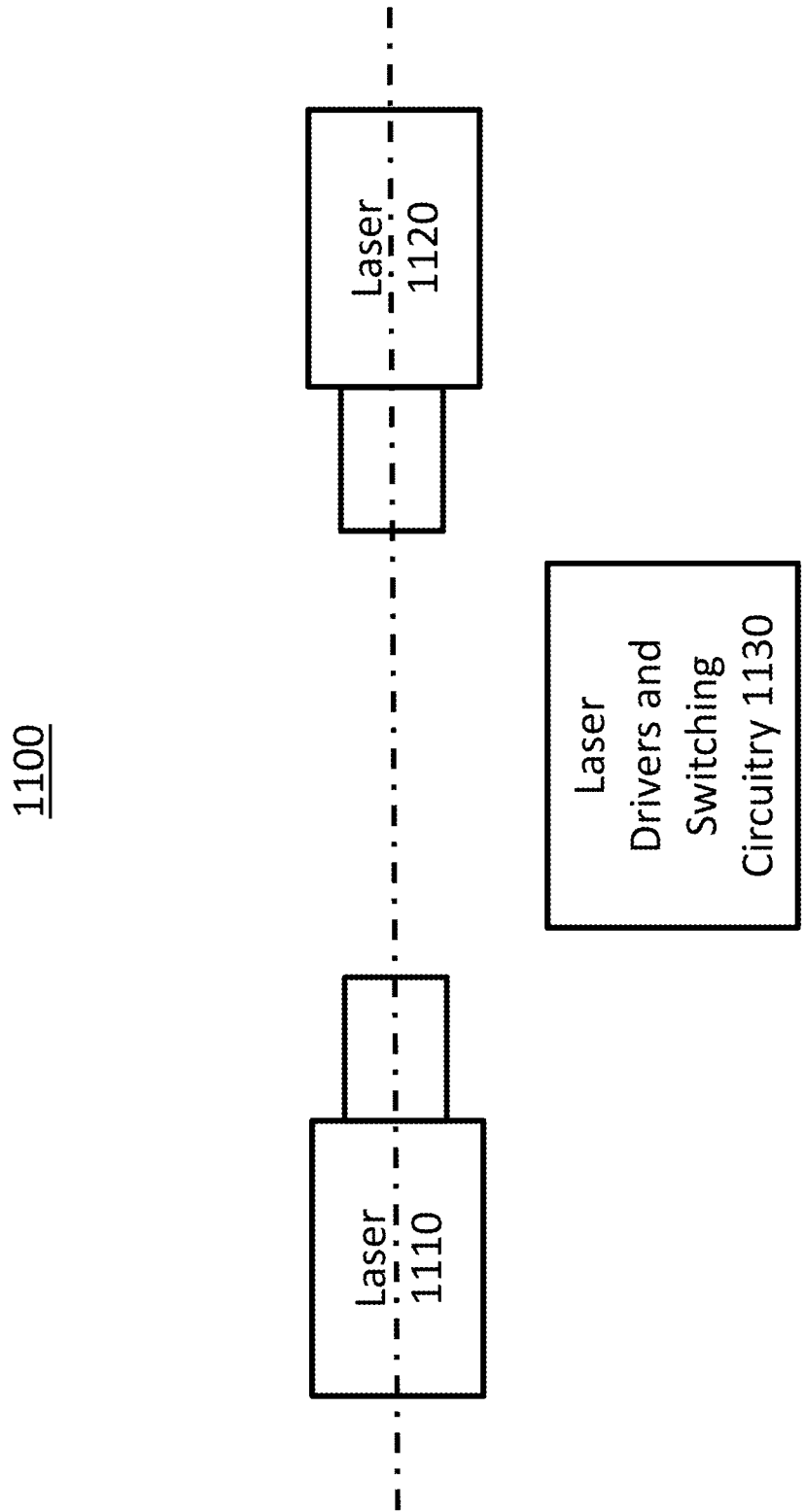
FIG. 11 is a simplified block diagram of an exemplary embodiment of an apparatus in accordance with the present disclosure for a speaker type application.

FIG. 11 shows an exemplary apparatus 1100, which includes two lasers 1110 and 1120, and laser driving and switching circuitry 1130. Lasers 1110 and 1120 are positioned to direct the laser beams towards each other and so that the axes of both beams are collinear. The co-linearity of the beams is essential for maximum efficiency of the photophoretic action. The lasers are separated by a medium such as air and can be substituted with any medium within which photophoretic action is desired to produce sound. The laser driving and switching circuitry 1130 operates the lasers so as to alternately activate the laser so that laser 1110 is on while 1120 is off and vice-versa. The switching on and off of each laser is performed at frequency f resulting in sound generated at frequency f. The on and off switching of the lasers generates an oscillating momentum transfer from the photons to the medium particles. The resulting vibrations produced in the medium generate a sound pressure wave.

Apparatus 1100 can be combined with controls to modify the sound properties such as frequency and loudness. Apparatus 1100 essentially is a speaker. The driver and switching circuitry 1130 can also be controlled by a processor. The processor converts sound data into properties such as sound frequency, intensity, and sound generation location that is transferred to driver and switching circuitry 1130 to control the lasers 1110 and 1120 to generate sound. The speaker can be used in various sound applications such as music and ultrasonic applications.

Figure 12A:
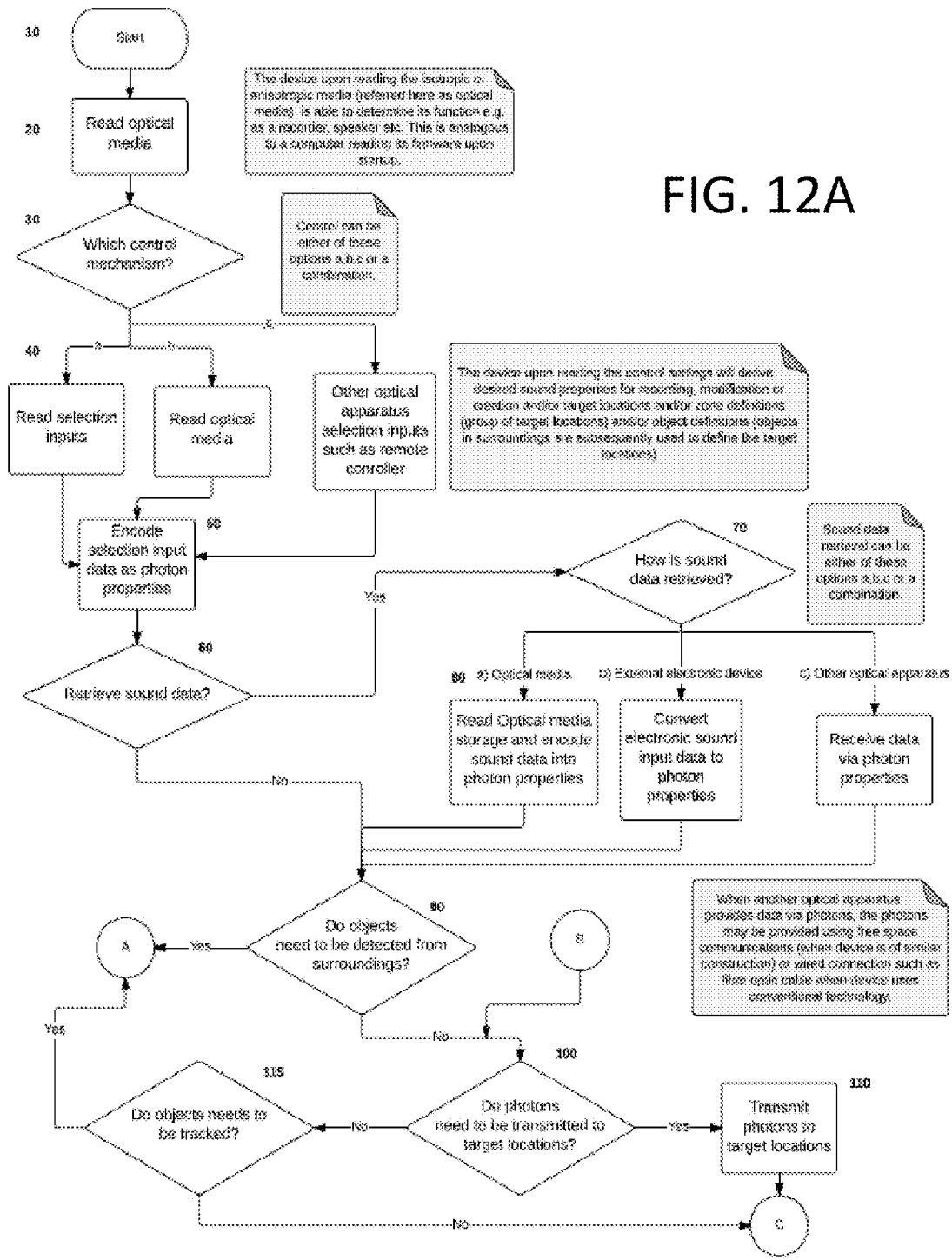
FIGS. 12A-12C show a flowchart illustrating various implementations in accordance with the present disclosure.
Figure 12B:
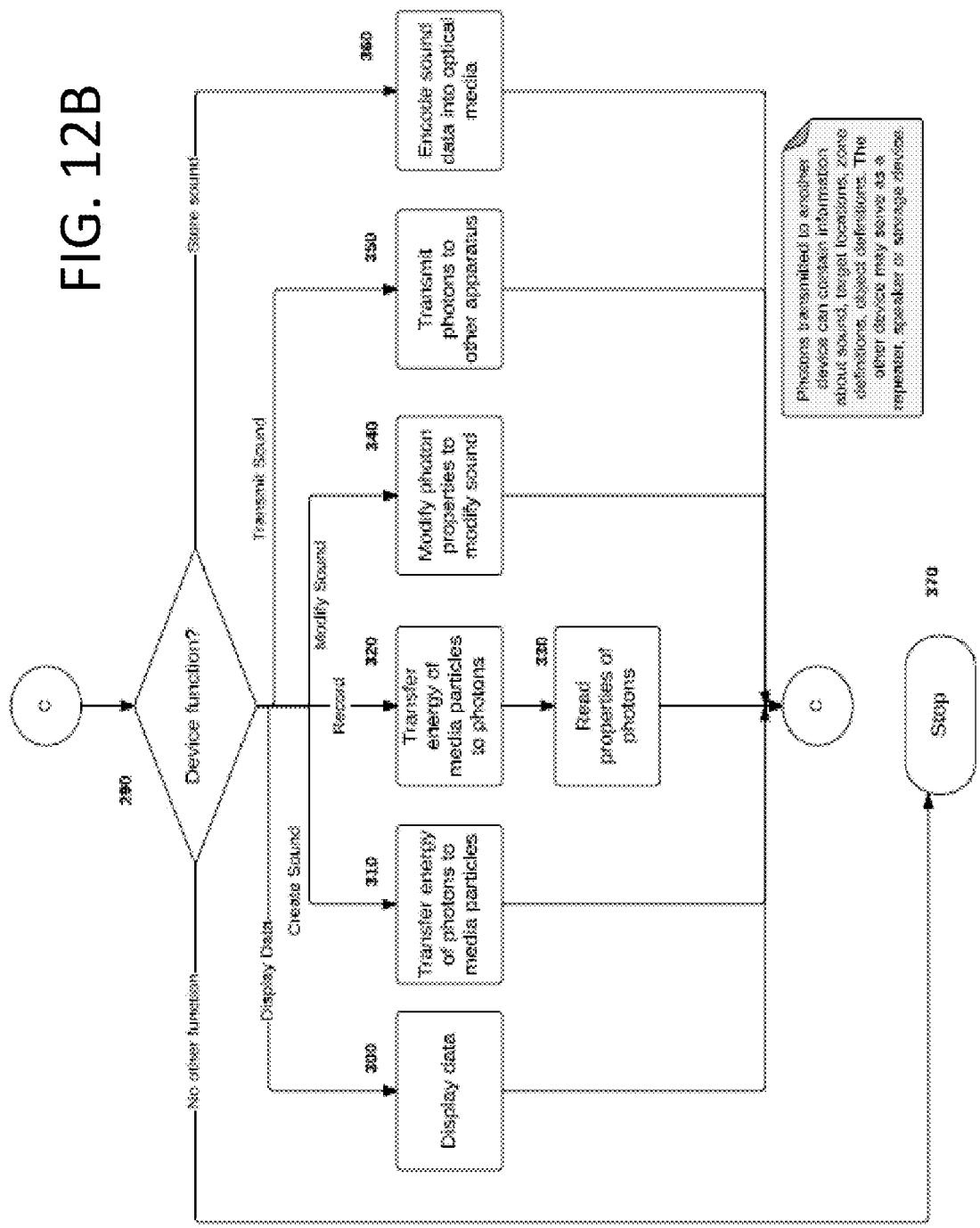
Figure 12C:
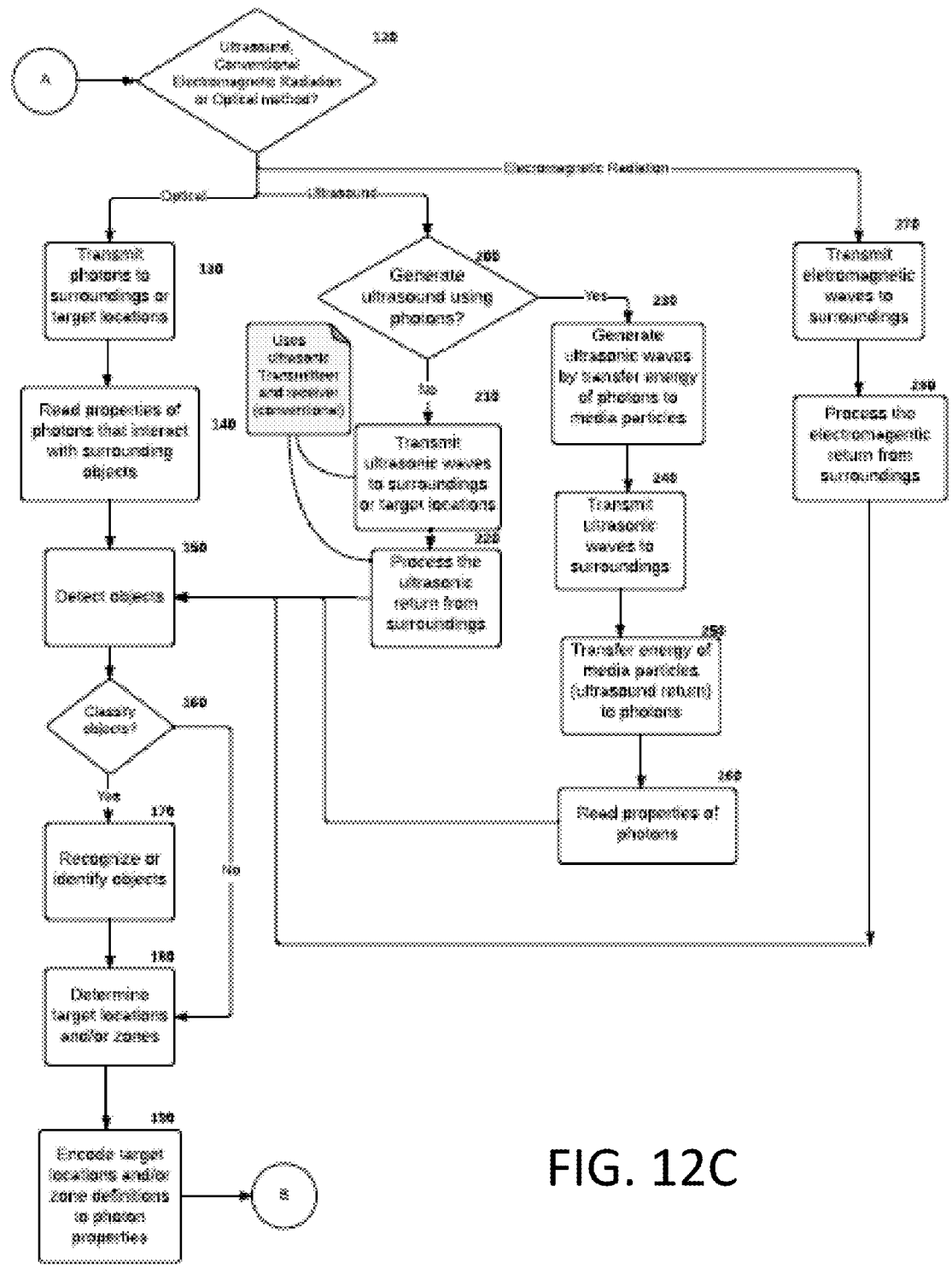

In an exemplary implementation in accordance with the present disclosure, an apparatus comprising orthogonal laser light sources and at least one isotropic or anisotropic medium is adapted to: detect one or more selection inputs provided by controls; encode the selection inputs as photon properties; transmit the photons to target locations, wherein one or more properties of the photons are affected by the transfer of energy from sound pressure waves to the photons; and detect the one or more properties of the photons thus affected. With reference to FIGS. 12A-12C, an exemplary implementation includes elements 10, 20, 30, 40a, 50, 60, 90, 100, 110 290, 320, 330, 290 and 370. Elements 40b and 40c may also be included. Additionally, object detection, recognition, identification and tracking (shown as Path A) can be included to track a user's mouth and to generate a recording zone in a microphone application. Implementations of such an apparatus can be used to replace, for example, conventional microphones, or ultrasonic receivers.

In another exemplary implementation in accordance with the present disclosure, an apparatus comprising orthogonal laser light sources and at least one isotropic or anisotropic medium is adapted to: detect one or more selection inputs provided by controls; read sound data encoded as photon properties from photons transmitted to the apparatus; modify the photon properties to modify the sound data based on the selection inputs; determine, via selection input, sound pressure wave creation target locations for transmission of sound information; transfer the sound information via photons to the target locations; and create sound pressure waves at the target locations by transferring photon energy to media particles at the target locations. With reference to FIGS. 12A-12C, an exemplary implementation includes elements 10, 20, 30, 40a, 50, 60, 70, 80c, 90, 100, 110, 290, 340, 290, 310, 290, and 370. Elements 40b and 40c may also be included. Elements 80a and 80b may also be included. Additionally, object detection, recognition, identification and tracking (shown as Path A) can be included to track a user's ears and to generate a sound creation zone in a speaker application. Implementations of such an apparatus can be used to replace, for example, conventional speakers, headphones or other such sound generating devices including conventional playback devices such as audio players, jukeboxes, or ultrasonic systems including transducers.

In another exemplary implementation in accordance with the present disclosure, an apparatus comprising orthogonal laser light sources and at least one isotropic or anisotropic medium is adapted to: detect one or more selection inputs provided by controls; determine target locations from selection inputs or optically encoded data; transmit photons to target locations; detect incoming sound pressure waves; transfer energy from the incoming sound pressure waves to photons; modify the photon properties based on the selection inputs optionally in order to modify the sound data; and store the sound information encoded in the photons in the isotropic or anisotropic medium. With reference to FIGS. 12A-12C, an exemplary implementation includes elements 10, 20, 30, 40a, 50, 60, 90, 100, 110, 290, 320, 320, 290, 340, 290, 360, 290, and 370. Elements 40b and 40c may also be included. Additionally, object detection, recognition, identification and tracking (shown as Path A) can be included to track a user's mouth and to generate a recording zone in a recording application. Implementations of such an apparatus can be used to replace, for example, conventional sound recorders with storage medium, or ultrasonic systems comprising ultrasonic receivers and data storage.

In another exemplary implementation in accordance with the present disclosure, an apparatus comprising orthogonal laser light sources and at least one isotropic or anisotropic medium is adapted to: detect one or more selection inputs provided by controls; optically read sound data encoded as photon properties that are transmitted to the apparatus from another apparatus; optionally modify the sound data in accordance with the selection input; and store the sound information encoded in the photons in the isotropic or anisotropic medium. With reference to FIGS. 12A-12C, an exemplary implementation includes elements 10, 20, 30, 40a, 50, 60, 70, 80c, 90, 100, 110, 290, 340, 290, 360, 290, and 370. Elements 40b and 40c may also be included. Elements 80b may also be included. Implementations of such an apparatus can be used to replace, for example, conventional sound recorders that receive audio data via a wired or wireless connection.

In yet another exemplary implementation in accordance with the present disclosure, an apparatus comprising orthogonal laser light sources and at least one isotropic or anisotropic medium is adapted to: detect one or more selection inputs provided by controls; read optically encoded sound data in photons that are transmitted to the apparatus from another apparatus; modify the sound data in accordance with the selection input; identify target locations or apparatuses for transmission of sound information via the selection inputs; transfer photons to the target sound pressure wave creation locations or apparatuses; and transfer photon energy to media particles at the target locations. With reference to FIGS. 12A-12C, an exemplary implementation includes elements 10, 20, 30, 40a, 50, 60, 70, 80c, 90, 100, 110, 290, 340, 290, 310, 290, 370. Elements 40b and 40c may also be included. Elements 80a and 80b may also be included. Implementations of such an apparatus can be used to replace, for example, conventional synthesizers, karaoke devices, audio repeaters, or mixing and mastering devices.

In another exemplary implementation in accordance with the present disclosure, an apparatus comprising orthogonal laser light sources and at least one isotropic or anisotropic medium is adapted to: detect one or more selection inputs provided by controls, transfer photons to the target sound pressure wave recording locations, detect incoming sound pressure waves, transfer energy from incoming sound pressure waves into photon energy, transfer the energy in the photons into visual displayable information, and store the optically encoded sound data in the isotropic or anisotropic medium. With reference to FIGS. 12A-12C, an exemplary implementation includes elements 10, 20, 30, 40a, 50, 60, 90, 100, 110, 290, 320, 330, 290, 300, 290, 360, 290, and 370. Elements 40b and 40c may also be included. Additionally, object detection, recognition, identification and tracking (shown as Path A) can be included to locate objects of interest and to generate a recording zone. Implementations of such an apparatus can be used to replace, for example, conventional phonometers.

In another exemplary implementation in accordance with the present disclosure, an apparatus comprising orthogonal laser light sources and at least one isotropic or anisotropic medium is adapted to: detect one or more selection inputs provided by controls, modify the sound information carried by photons originating in the device based on the selection input(s), identify target locations or apparatuses for transmission of sound information, transfer the sound information via photons to the target sound pressure wave creation locations or apparatuses, and generate sound at the target sound pressure wave creation locations by transferring photon energy to energy of media particles. With reference to FIGS. 12A-12C, an exemplary implementation includes elements 10, 20, 30, 40a, 50, 60, 90, 100, 110 290, 350, 290, 310, 290, and 370. Element 40c may also be included. Additionally, object detection, recognition, identification and tracking (shown as Path A) can be included to track a user's ears and to generate a sound creation zone. Implementations of such an apparatus can be used to replace, for example, conventional musical instruments with speaker or audio transmission systems.

In another exemplary implementation in accordance with the present disclosure, an apparatus comprising orthogonal laser light sources and at least one isotropic or anisotropic medium is adapted to: detect one or more selection inputs provided by controls that are associated with one or more sound sources, read optically encoded sound data from the isotropic or anisotropic medium, read optically encoded sound data in photons that are transmitted to the apparatus from one or more other apparatuses, use the selection input to modify the photon properties in order to modify the sound data for each sound source, store the combined sound data in the isotropic or anisotropic medium, identify target apparatuses for transmission of sound information, and transfer the sound information via photons to the apparatuses. With reference to FIGS. 12A-12C, an exemplary implementation includes elements 10, 20, 30, 40a, 50, 60, 70, 80a, 80c, 90, 100, 110 290, 340, 290, 360, 290, 350, 290, and 370. Elements 40b and 40c may also be included. Element 80b may also be included. Implementations of such an apparatus can be used to replace, for example, conventional mixers or digital sound workstations.

In another exemplary implementation in accordance with the present disclosure, an apparatus comprising orthogonal laser light sources and at least one isotropic or anisotropic medium is adapted to: detect one or more selection inputs provided by controls, transmit photons to target locations determined from the selection inputs, detect photons returned from target locations and surroundings and identify photon properties, process the returned photon data using optical computing, from the processed data detect objects, and classify the detected objects into known objects such as human body parts (ears, nose, or head), man-made and natural objects (windows, walls, or trees). The apparatus may be further adapted to determine target sound pressure wave creation locations, and/or perform object identification based on the detected objects. With reference to FIGS. 12A-12C, an exemplary implementation includes elements 10, 20, 30, 40a, 50, 60, 90, 120, 130, 140, 150, 160, 170, 180, 190,100, 115, 290, and 370. Elements 40b and 40c may also be included.

In another exemplary implementation in accordance with the present disclosure, an apparatus comprising orthogonal laser light sources, at least one isotropic or anisotropic medium and integrated with an electronics based ultrasonic transmitter, receiver and electronic processor, is adapted to: detect one or more selection inputs provided by controls, transmit ultrasonic waves from the ultrasonic transmitter, process the ultrasonic return using the electronic processor, detect, classify and identify surrounding objects using the processor, and determine the target locations based on the input(s). With reference to FIGS. 12A-12C, an exemplary implementation includes elements 10, 20, 30, 40a, 50, 60, 90, 120, 200, 210, 220, 150, 160, 170, 180, 190, 100, 110, 290, 370. Elements 40b and 40c may also be included.

In another exemplary implementation in accordance with the present disclosure, an apparatus comprising orthogonal laser light sources, at least one isotropic or anisotropic medium and integrated with an electronics based radiofrequency transmitter, receiver and electronic processor, is adapted to: detect one or more selection inputs provided by controls, transmit radiofrequency waves from the radiofrequency transmitter, process the radiofrequency return using the electronic processor, detect, classify and identify surrounding objects using the processor, and determine the target locations based on the input(s). With reference to FIGS. 12A-12C, an exemplary implementation includes elements 10, 20, 30, 40a, 50, 60, 90, 120, 200, 210, 220, 150, 160, 170, 180, 190, 100, 110, 290, and 370. Elements 40b and 40c may also be included.

In another exemplary implementation in accordance with the present disclosure, an apparatus comprising orthogonal laser light sources and at least one isotropic or anisotropic medium is adapted to: obtain information defining one or more zones, said information being provided by one or more selection inputs of controls; transmit photons to the target locations defining zone boundaries or volume; determine sound properties of the zone from the selection inputs; and transfer energy of media particles to photons for only the sound pressure waves that originate within the zone. With reference to FIGS. 12A-12C, an exemplary implementation includes elements 10, 20, 30, 40a, 50, 60, 90, 100, 110, 290, 320, 330, 290, and 370. Elements 40b and 40c may also be included. Additionally, object detection, recognition, identification and tracking (shown as Path A) can be included to track a user's mouth or detect room walls and to generate a recording zone. Implementations of such an apparatus can be used to replace, for example, conventional windscreens or sound recording rooms.

In another exemplary implementation in accordance with the present disclosure, an apparatus comprising orthogonal laser light sources and at least one isotropic or anisotropic medium is adapted to: obtain information defining one or more zones and sound properties of the zone, said information being provided by one or more selection inputs of controls; transmit photons to the zone boundaries or volume; and use the sound properties to modify sound pressure waves traveling through the defined zone by the exchange of energy between media particles and photons. With reference to FIGS. 12A-12C, an exemplary implementation includes elements 10, 20, 30, 40a, 50, 60, 90, 100, 110, 290, 340, 290, 310, 290, and 370. Elements 40b and 40c may also be included. Additionally, object detection, recognition, identification and tracking (shown as Path A) can be included to detect or track objects that define a sound manipulation zone. In an exemplary implementation, the exchange of energy takes place at the boundaries of a zone so that the resulting sound in the zone is in accordance with the selected properties, such as, for example, a silence zone where no sound reaches. A zone volume may also be defined so that a gradient of sound properties may be formed, such as, for example, a gradual increase in sound pressure level within the volume so that energy exchange is not limited to the boundaries of the zone but also occurs across the zone volume. Implementations of such an apparatus can be used to replace, for example, conventional soundproofing materials, or noise reduction devices.

In another exemplary implementation in accordance with the present disclosure, an apparatus comprising orthogonal laser light sources and at least one isotropic or anisotropic medium is adapted to: obtain information defining one or more zones, said information being provided by one or more selection inputs of controls; modify the properties of photons generated by the device based on the information; transfer photons to the zone boundaries or volume; and generate sound pressure waves only in the zone by transferring energy from photons to media particles. With reference to FIGS. 12A-12C, an exemplary implementation includes elements 10, 20, 30, 40a, 50, 60, 70, 80a, 90, 100, 110, 290, 340, 290, 310, 290, and 370. Elements 40b and 40c may also be included. Elements 80a and 80b may also be included. Additionally, object detection, recognition, identification and tracking (shown as Path A) can be included to detect or track objects that define a sound creation zone. Implementations of such an apparatus can be used to replace, for example, conventional speaker arrays that produce audio zones.

In another exemplary implementation in accordance with the present disclosure, an apparatus comprising orthogonal laser light sources and at least one isotropic or anisotropic medium is adapted to: obtain information defining one or more types of objects and target locations, said information being provided by one or more selection inputs of controls; transmit photons to the target locations; process the photon properties after their interaction with the object (such as by using optical computing) to determine if the defined object types are found, determine target locations from detected objects, and encode location properties as photon properties. With reference to FIGS. 12A-12C, an exemplary implementation includes elements 10, 20, 30, 40a, 50, 60, 90, 120, 130, 140, 150, 160, 170, 180, 190, 100, 115, 290, and 370. Elements 40b and 40c may also be included. Implementations of such an apparatus can be used to replace, for example, conventional video cameras and systems performing object recognition and identification.

In another exemplary implementation in accordance with the present disclosure, an apparatus comprising orthogonal laser light sources and at least one isotropic or anisotropic medium is adapted to: obtain information defining one or more zones, sound properties and target locations, said information being provided by one or more selection inputs of controls; modify the properties of device generated photons based on the information; transfer photons to the target locations, generate sound pressure waves at target locations by transferring photon energy to media particles when a defined object or object type (living or non-living) is detected in a certain location with respect to the defined zone such as when the object crosses the defined zone boundary; and storing the object type properties and time data in the isotropic or anisotropic medium. With reference to FIGS. 12A-12C, an exemplary implementation includes elements 10, 20, 30, 40a, 50, 60, 70, 80a, 90, A (any branch), B, 100, 115, 100, 110, 290, 310, 290, and 370. Elements 40b and 40c may also be included. Elements 80a and 80b may also be included. Continuous object tracking is implemented by repeating the sequence: path A, path B, element 100, and element 115. Implementations of such an apparatus can be used to replace, for example, conventional motion detectors.

In another exemplary implementation in accordance with the present disclosure, an apparatus comprising orthogonal laser light sources and at least one isotropic or anisotropic medium is adapted to: obtain information defining one or more zones and noise rejection properties of the zones, said information being provided by one or more selection inputs of controls; transfer photons to the zones, determine and characterize the noise within, surrounding, or at the boundaries of the zones by transferring some or all of the media particle energy to photons; and generate sound pressure waves within, surrounding or at the boundary of the defined volumes by transferring energy from media particles to photons, resulting in cancellation of the noise within, surrounding, or at the boundaries of the zones in accordance with the defined noise rejection properties. With reference to FIGS. 12A-12C, an exemplary implementation includes elements 10, 20, 30, 40a, 50, 60, 90, 100, 110, 290, 320, 330, 290, 340, 290, 310, 290, and 370. Elements 40b and 40c may also be included. Additionally, object detection, recognition, identification and tracking (shown as Path A) can be included to detect or track a user's ears that define a noise cancellation zone. Implementations of such an apparatus can be used to replace, for example, conventional active noise-cancellation devices.

In another exemplary implementation in accordance with the present disclosure, an apparatus comprising orthogonal laser light sources and at least one isotropic or anisotropic medium is adapted to: obtain information defining one or more zones and noise rejection properties of the zones, said information being provided by one or more selection inputs of controls; transfer photons to the zones, transfer energy from photons to media particles to modify the distance of media particles from each other resulting in modified sound in accordance with the defined noise rejection properties. With reference to FIGS. 12A-12C, an exemplary implementation includes elements 10, 20, 30, 40a, 50, 60, 90, 100, 110, 290, 320, 330, 290, 340, 290, 310, 290, and 370. Elements 40b and 40c may also be included. Additionally, object detection, recognition, identification and tracking (shown as Path A) can be included to detect or track an object such as user's ears or room walls that define a noise cancellation zone. Implementations of such an apparatus can be used to replace, for example, conventional noise reduction materials and devices.

In another exemplary implementation in accordance with the present disclosure, an apparatus comprising orthogonal laser light sources and at least one isotropic or anisotropic medium is adapted to: obtain information defining ultrasonic pressure wave properties and target pressure wave generation locations, said information being provided by one or more selection inputs of controls; and generate an ultrasonic pressure wave by transferring photonic energy to media particles at the target locations. With reference to FIGS. 12A-12C, an exemplary implementation includes elements 10, 20, 30, 40a, 50, 60, 90, 100, 110, 290, 310, 290, and 370. Elements 40b and 40c may also be included. Elements 80a, 80b and 80c may also be included to receive ultrasonic wave data properties. Additionally, object detection, recognition, identification and tracking (shown as Path A) can be included to detect or track objects that define a target ultrasound generation zone. Implementations of such an apparatus can be used to replace, for example, conventional ultrasonic devices for heating, welding, soldering, and humidification.

In another exemplary implementation in accordance with the present disclosure, an apparatus comprising orthogonal laser light sources and at least one isotropic or anisotropic medium is adapted to: obtain information defining ultrasonic pressure wave properties and target pressure wave generation locations, said information being provided by one or more selection inputs of controls; and generate an ultrasonic pressure wave by transferring photonic energy to media particles at the target locations. The energy of ultrasonic pressure waves reflected by or transmitted through one or more objects at the target locations is transferred from media particles to photons. The apparatus is further adapted to determine one or more properties of one or more objects by processing the photons that exchanged energy with the reflected and/or transmitted ultrasonic pressure waves, such as by using photon based processing, store this information in the isotropic or anisotropic medium, and transmit this information to a display system, such as via photons. With reference to FIGS. 12A-12C, an exemplary implementation includes elements 10, 20, 30, 40a, 50, 60, 90, 120, 200, 230, 240, 250, 260, 150, 160, 170, 180, 190, 100, 110, 290, 360, 290, 300, 290, and 370. Elements 40b and 40c may also be included. Elements 80a, 80b and 80c may also be included to receive ultrasonic wave data properties. Elements 210 and 220 may also be included in place of 230, 240, 250 and 260. Additionally, object detection, recognition, identification and tracking (shown as Path A) can be included to detect or track objects that define a target ultrasound generation zone. Implementations of such an apparatus can be used to replace, for example, conventional ultrasonic devices for imaging, metal flaw detection, parking assist, and liquid level measurement. Elements 150, 160 and 170 pertain to classification of ultrasonic return, for e.g., determination of high vs. low echogenicity, anisotropy, blood flow speed and direction and determining a tumor vs. tissue.

| TABLE OF ACRONYMS | |
|---|---|
| 2-D, 3-D, 4-D | 2-dimensional, 3-dimensional, 4-dimensional |
| MEMS | Micro Electro Mechanical Systems |
| FLAC | Free Lossless Audio Codec |
| ALAC | Apple Lossless Audio Codec |
| HDMI | High Definition Multimedia Interface |
| LCRS | Left, Center, Right and Surround |
| MIDI | Musical Instrument Digital Interface |
| OSC | Open Sound Control |
| CPU | Central Processing Unit |
| dB | Decibel |
| ANC | Active Noise Control |
| RMS | Root Mean Square |
| CMUT | Capacitive Micro machined Ultrasonic Transducers |
| SNR | Signal to Noise Ratio |
| UBM | Ultrasonic BioMicroscope |
| ARFI | Acoustic Radiation Force Impulse |
| HMI | Harmonic Motion Imaging |
| SSI | Supersonic Shear Imaging |
| SMURF | Spatially Modulated Ultrasound Radiation Force |
| EMAT | ElectroMagnetic Acoustic Transducers |
| SPL | Sound Pressure Level |
| HRTF | Head Related Transfer Function |

As per this disclosure, the example aspects above can be combined in any manner to enhance functionality of the apparatus. The invention is not limited to these example aspects. The invention is applicable to any of a variety of sound generating, modifying, distributing and receiving methods and apparatuses.

While this disclosure has been presented using some specific examples, those skilled in the art will recognize that the teachings of this disclosure are not thus limited. Accordingly, this disclosure should be only limited by the scope of the claims attached hereto.

What is claimed is:

1. An apparatus comprising:
   a medium, the medium being isotropic or anisotropic and having photorefractive properties;
   a first coherent source of photons; and
   a second coherent source of photons,
   wherein the first and second coherent sources of photons are arranged so that photon beams emitted therefrom are directed onto the medium mutually orthogonally, and photons are directed from the medium to target media particles of a target medium outside the medium wherein the target media particles are not in contact with the medium.

2. The apparatus of claim 1 comprising an input signal source, the input signal source including at least one of a selection input of a control, the medium, a storage medium and a remote apparatus.

3. The apparatus of claim 2, wherein the input signal indicates a target location in the target medium to which photons are to be transmitted from the medium, the photons being directed to the target location non-mechanically.

4. The apparatus of claim 2, wherein the input signal indicates one or more properties of sound pressure waves to be generated, modified, or recorded by the apparatus in the target medium.

5. The apparatus of claim 2, wherein the input signal indicates one or more properties of material objects to be located by the apparatus.

6. The apparatus of claim 1, wherein the medium includes at least one of a crystal, a liquid crystal, a photonic crystal, gallium arsenide (GaAs), barium titanate ($BaTiO_3$), lithium niobate ($LiNbO_3$), bismuth silicon oxide ($Bi_{12}SiO_{20}$), potassium niobate ($KNbO_3$), strontium niobate ($SrNb_2O_6$), a polymer, a polymer composite, an amorphous composite, a dielectric, or a semiconductor.

7. The apparatus of claim 1 comprising a processor.

8. The apparatus of claim 7, wherein the processor is an optical processor.

9. A method comprising:
   determining a target location;
   transmitting from a first medium, photons to the target location, whereby energy is transferred between the photons and target media particles of a second medium at the target location thereby affecting at least one property of the photons, wherein the first medium is photorefractive, the target location is external to the first medium, and the target media particles are not in contact with the first medium; and
   detecting the at least one affected property of the photons using dynamic holography to transfer information from the photons to the first medium.

10. The method of claim 9, wherein the energy is characterized by a sound pressure wave, including at least one of an infrasound, audible sound and ultrasound sound pressure wave.

11. The method of claim 10 comprising recording the sound pressure wave in accordance with the detected at least one property of the photons.

12. The method of claim 9, comprising locating one or more material objects, wherein the target location is determined in accordance with the one or more material objects located.

13. A method comprising:
   affecting in accordance with an input signal at least one property of photons for transmission from a first medium, including using dynamic holography to transfer information from the first medium to the photons;
   determining a target location;
   transmitting the photons with the at least one affected property to the target location, whereby energy is transferred between the photons and target media particles of a second medium at the target location thereby affecting one or more properties of the target media particles in accordance with the input signal, wherein the first medium is photorefractive, the target location is external to the first medium, and the target media particles are not in contact with the first medium.

14. The method of claim 13, wherein the energy is characterized by a sound pressure wave, including at least one of an infrasound, audible sound and ultrasound sound pressure wave.

15. The method of claim 14 comprising generating the sound pressure wave at the target location in accordance with the input signal.

16. The method of claim 15, wherein generating the sound pressure wave at the target location includes at least one of setting a loudness, frequency spectrum, pitch, echo, delay, reverberation, phase, distortion, noise level, filtering profiles and Doppler amount of the sound pressure wave.

17. The method of claim 13 comprising modifying a pre-existing sound pressure wave at the target location in accordance with the input signal.

18. The method of claim 17, wherein modifying the sound pressure wave at the target location includes at least one of altering a loudness, frequency spectrum, pitch, echo, delay, reverberation, phase, distortion, noise level, filtering profiles and Doppler amount of the sound pressure wave.

19. The method of claim 13 comprising receiving the input signal from at least one of a selection input of a control, a storage medium, and a remote apparatus.

20. The method of claim 13 comprising locating one or more material objects, wherein the target location is determined in accordance with the one or more material objects located.

* * * * *